United States Patent
Kanda

(10) Patent No.: US 11,773,169 B2
(45) Date of Patent: Oct. 3, 2023

(54) THERAPEUTIC AGENT TARGETED TO RECEPTOR PROTEIN, TEST AGENT, ANTIBODY THAT BINDS TO RECEPTOR PROTEIN, AND SCREENING METHOD FOR MOLECULARLY TARGETED DRUGS

(71) Applicant: YMMUNOBIO AG, Riehen (CH)

(72) Inventor: Mitsuro Kanda, Aichi (JP)

(73) Assignee: YMMUNOBIO AG, Riehen (CH)

( * ) Notice: Subject to any disclaimer, the term of this patent is extended or adjusted under 35 U.S.C. 154(b) by 0 days.

(21) Appl. No.: 16/964,236

(22) PCT Filed: Jan. 25, 2019

(86) PCT No.: PCT/JP2019/002504
§ 371 (c)(1),
(2) Date: Jul. 23, 2020

(87) PCT Pub. No.: WO2019/146759
PCT Pub. Date: Aug. 1, 2019

(65) Prior Publication Data
US 2021/0040208 A1    Feb. 11, 2021

(30) Foreign Application Priority Data
Jan. 26, 2018 (JP) .................. 2018-011937

(51) Int. Cl.
| C07K 16/28 | (2006.01) |
| A61P 35/04 | (2006.01) |
| C12N 15/113 | (2010.01) |
| G01N 33/574 | (2006.01) |
| A61K 39/00 | (2006.01) |

(52) U.S. Cl.
CPC ............ *C07K 16/286* (2013.01); *A61P 35/04* (2018.01); *C12N 15/1138* (2013.01); *G01N 33/57407* (2013.01); *G01N 33/57415* (2013.01); *G01N 33/57419* (2013.01); *G01N 33/57423* (2013.01); *G01N 33/57438* (2013.01); *G01N 33/57446* (2013.01); *G01N 33/57492* (2013.01); *A61K 2039/505* (2013.01); *C07K 2317/34* (2013.01); *C07K 2317/76* (2013.01); *C12N 2310/141* (2013.01)

(58) Field of Classification Search
CPC ... C07K 16/286; A61P 35/04; C12N 15/1138; G01N 33/57407; G01N 33/57415; G01N 33/57419; G01N 33/57423; G01N 33/57438; G01N 33/57446; G01N 33/57492
See application file for complete search history.

(56) References Cited

U.S. PATENT DOCUMENTS

| 2005/0032155 A1 | 2/2005 | Philips et al. | |
| 2005/0037445 A1* | 2/2005 | Poulsen | C12Q 1/6809 435/7.23 |
| 2009/0123940 A1 | 5/2009 | Worley et al. | |
| 2010/0136623 A1 | 6/2010 | Mulley et al. | |
| 2011/0152345 A1* | 6/2011 | Nakamura | G01N 33/57423 514/44 A |
| 2017/0157245 A1 | 6/2017 | Dupont | |

FOREIGN PATENT DOCUMENTS

| JP | 2003-533229 A | 11/2003 |
| JP | 2010-536366 A | 12/2010 |
| JP | 2017-511342 A | 4/2017 |
| WO | 2012/153492 A1 | 11/2012 |

OTHER PUBLICATIONS

Bartolini et al., "The Neuronal Pentraxin-2 Pathway Is an Unrecognized Target in Human Neuroblastoma, Which Also Offers Prognostic Value in Patients", Cancer Res. Oct. 15, 2015;75(20):4265-71 (Year: 2015).*
Bartolini et al. "The Neuronal Pentraxin-2 Pathway Is an Unrecognized Target in Human Neuroblastoma, Which Also Offers Prognostic Value in Patients", Cancer research 75.20: 4265-71 (2015). (cited in IDS) (Year: 2015).*
The Merck Manuals Online Medical Library, [online]. Merck Research Laboratories, 2006-2007. [retrieved on Oct. 19, 2020]. < URL: https://www.merckmanuals.com/professional/hematology-and-oncology/overview-of-cancer/cellular-and-molecular-basis-of-cancer >. Cellular and Molecular Basis of Cancer (Year: 2020).*
Kotteas et al. "Immunotherapy for pancreatic cancer", Journal of Cancer Research & Clinical Oncology, 142.8: 1795-1805. (Year: 2016).*
Li-Lian et al., "Molecular Mechanisms and Potential Therapeutic Reversal of Pancreatic Cancer-Induced Immune Evasion", Cancers 12.7: 1872 (Year: 2020).*
M. Apicella, et al., "Targeted therapies for gastric cancer: failures and hopes from clinical trials," Oncotarget, 2017, vol. 8, No. 34, p. 57654-57669 (cited in specification).
H. Ohnuma, "Chemotherapy for metastatic or recurrent gastric cancer," The Hokkaido Journal of Surgery, Jun. 2017, vol. 62, No. 1, 121 pgs., with summary in English language on p. 28 (cited in specification).

(Continued)

*Primary Examiner* — Amy E Juedes
*Assistant Examiner* — Peter Johansen
(74) *Attorney, Agent, or Firm* — FOX ROTHSCHILD LLP

(57) ABSTRACT

From gene expression analysis with a long-term recurrence-free group and a recurrence metastasis group of stomach cancer, CHRNB2 and NPTXR were identified as drug discovery targets. Tumor growth was successfully inhibited by an antibody medicine or a nucleic acid medicine targeting CHRNB2 or NPTXR. Furthermore, a polyclonal antibody and a monoclonal antibody linking to CHRNB2 or NPTXR are provided. Since these receptor molecules are novel molecular targets, treatment of cases which the existing therapeutic drugs have no effect on is made possible.

6 Claims, 25 Drawing Sheets

Specification includes a Sequence Listing.

(56) References Cited

OTHER PUBLICATIONS

A. Bartolini, et al., "The Neuronal Pentraxin-2 Pathway Is an Unrecognized Target in Human Neuroblastoma, Which Also Offers Prognostic Value in Patients," American Association for Cancer Research, Oct. 15, 2015, vol. 75, No. 20, pp. 4265-4271 (cited in specification).
English translation of International Preliminary Report on Patentability issued in corresponding International Application No. PCT/JP2019/002504, dated Jun. 5, 2020.
I. W. Jones, et al., "Presynaptic Localisation of the Nicotinic Acetylcholine Receptor Beta 2 Subunit Immunoreactivity in Rat Nigrostriatal Dopaminergic Neurons," The Journal of Comparative Neurology, 2001, vol. 439, pp. 235-247 (cited in IPRP).
Yin G N et al: "Neuronal pentraxin receptor in cerebrospinal fluid as a potential biomarker for neurodegenerative diseases", Brain Research, Else Vier, Amsterdam, NL, vol. 1265, Apr. 10, 2009 (Apr. 10, 2009), pp. 158-170, XP026075028, ISSN: 0006-8993, DOI: 10.1016/J.BRAINRES.2009.01.058 [retrieved on Feb. 6, 2009].
Dodds et al: "Neuronal pentraxin receptor, a novel putative integral membrane pentraxin that interacts with neuronal pentraxin 1 and 2 and taipoxin-associated calcium-binding protein 49", Journal of Biological Chemistry, American Society for Biochemistry and Molecular Biology, US, vol. 272, No. 34, Aug. 22, 1997 (Aug. 22, 1997), pp. 21488-21494, XP002140646, ISSN: 0021-9258, DOI: 10.1074/JBC.272.34.21488.
Still, P. C. et al.: "Alkaloids from microcos paniculata with cytotoxic and nicotinic receptor antagonistic activities", Journal of Natural Products, vol. 76, 2013, pp. 243-249, XP055631030, DOI: 10.1021/np3007414.
The extended European search report issued in related EP Application No. 19744055.5, dated Mar. 18, 2022.
Office Action issued in corresponding Chinese Application 201980022443.1 dated Jun. 20, 2022, with English translation (17 pages).
Chinese Office Action and English Translation dated Jan. 13, 2023 in CN Application No. 201980022443.1.
Chen Zhihong et al: "Original Article Mutational analysis of CHRNB2, CHRNA2 and CHRNA4 genes in Chinese population with autosomal dominant nocturnal frontal lobe epilepsy", Int J Clin Exp Med, Jan. 1, 2015.
Extended European Search Report dated Mar. 28, 2023 in EP 22196119.6.
Chinese Office Action dated May 22, 2023 in CN Application No. 201980022443.1.

\* cited by examiner

Figure 18D  NPTXR NEGATIVE CASE                    NPTXR POSITIVE CASE

THERAPEUTIC AGENT TARGETED TO RECEPTOR PROTEIN, TEST AGENT, ANTIBODY THAT BINDS TO RECEPTOR PROTEIN, AND SCREENING METHOD FOR MOLECULARLY TARGETED DRUGS

CROSS-REFERENCE OF RELATED APPLICATION

This application is the U.S. National Phase under 35 U.S.C. § 371 of International Patent Application No. PCT/JP2019/002504, filed on Jan. 25, 2019, which in turn claims the benefit of Japanese Application No. 2018-011937, filed on Jan. 26, 2018, the entire disclosures of which Applications are incorporated by reference herein.

SEQUENCE LISTING

The instant application contains a Sequence Listing which has been submitted electronically in ASCII format and is hereby incorporated by reference in its entirety. Said ASCII copy, created on Jul. 21, 2020, is named "Sequence_listing_MS17089_ST25.TXT" and is 2.70 KB in size.

TECHNICAL FIELD

The present invention relates to a therapeutic drug and a test reagent targeting a receptor protein. The present invention relates to a target medicine targeting a receptor expressing at a high level on a cancer cell surface and a signaling system responsible for signaling of the downstream of the receptor, in particular, an antibody medicine and a nucleic acid medicine against a receptor protein. Furthermore, the present invention relates to a companion diagnostics used in administration of the above molecular target drug or a test reagent used for forecasting prognosis such as recurrence. Further, the present invention relates to a method of screening a medicine targeting a receptor protein.

BACKGROUND ART

Stomach cancer is a cancer with the fourth highest number of cases and the second highest cancer-related number of deaths throughout the world (statistics in 2012). Stomach cancer is a common cancer in Asian countries such as Japan, China, Korea, and the like and South America, and according to statistics of Japanese cancer patients, the number of new stomach cancer cases is 133,000 (third most) and the mortality is 49,400 (third most) (statistics in 2015), that is, the incidence rate is high, and stomach cancer is a serious disease that should be overcome with priority.

In Japan, the mortality of stomach cancer tends to decrease because instances of early detection have increased due to spread of cancer screening. However, since substantially no symptom is found in an early-stage stomach cancer, a stomach cancer is still often detected after developed to an advanced stomach cancer, which causes a high mortality. As a primary treatment for an unresectable advanced recurrence stomach cancer, combined therapy of S-1 (tegafur, gimeracil, and oteracil potassium compounding agent) and cisplatin is established as a standard therapy in Japan. Furthermore, trastuzumab that is an anti-HER2 antibody is a standard therapeutic drug against an HER2 positive case. Further, as a secondary treatment, ramucirumab that is an anti-VEGFR-2 antibody and, furthermore, nivolumab that is an anti-PD-1 antibody, which is an immune checkpoint inhibitor, are approved (non-Patent Literatures 1 and 2).

Since the conventional anticancer agent aims to kill cancer cells by cell injury while a molecular target drug such as an antibody drug targets molecules excessively expressing in cancer cells, the action mechanisms thereof differ from each other. As a result, there is a high likelihood that the effect can also be obtained for patients who have not obtained the effect. Also for a molecular target therapeutic drug against stomach cancer, a new antibody medicine has been developed (Patent Literature 1).

CITATION LIST

Patent Literature

Patent Literature 1: Japanese Patent Application Publication No. 2017-511342

Non Patent Literature

Non-Patent Literature 1: Apicella M., et al., Oncotarget. 2017, Vol. 8(34), p. 57654-57669. doi: 10.18632/oncotarget.14825. PMID: 28915702
Non-Patent Literature 2: Hiroyuki Ohnuma, The Hokkaido Journal of Surgery, 2017, Vol. 62, No. 1, p. 23-28
Non-Patent Literature 3: Bartolini, A., et al., 2015, Cancer Res. Vol. 75(20), p. 4265-4271

SUMMARY OF INVENTION

Technical Problem

However, only the agents that target limited growth factors such as HER2, VEGF, or the like can be currently used against advanced stomach cancer. The number of cases of HER2 positive stomach cancer is around 20% of that of the advanced and recurrence stomach cancers, and trastuzumab is effective only to the HER2 positive stomach cancers. Further, the response rate of nivolumab that is a newly approved immune checkpoint inhibitor also still remains at around 20%, which results in limitation of treatment. Further, ramucirumab approved in the treatment for advanced stomach cancers in the United States does not have so high a prolonging effect of prognostics. Thus, development of an inhibitor that may control progression of a stomach cancer from a completely different action mechanism is essential for improving a treatment outcome.

The object of the present invention is to identify a molecule involved in stomach cancer progression to find a molecule that may be a target and provide a target therapeutic drug. Further, it is considered that the same action mechanism has the effect on cancer cells as long as a targeted molecule expresses thereon, and it is therefore expected that the same effect can be provided against other cancers without being limited to a stomach cancer.

Solution to Problem

The present invention relates to a molecular target drug, an antibody, a test reagent, and a method of screening a molecular target drug below.
(1) A molecular target therapeutic drug containing a substance that neutralizes or inhibits expression of Cholinergic Receptor Nicotinic Beta 2 Subunit (CHRNB2) as an active ingredient.

(2) The molecular target therapeutic drug according to (1), wherein the active ingredient is an antibody or a nucleic acid.

(3) The molecular target therapeutic drug according to (1) or (2), wherein the active ingredient recognizes either WKPEEFDNMKKVRLPSKH (SEQ ID NO: 8) or TFLHSDHSAPSSK (SEQ ID NO: 9) of CHRNB2.

(4) The molecular target therapeutic drug according to (3), wherein the active ingredient is an antibody.

(5) The molecular target therapeutic drug according to (4), wherein the antibody is produced by a hybridoma represented by Accession No. NITE P-02857.

(6) The molecular target therapeutic drug according to (1) or (2), wherein the active ingredient is a siRNA, a miRNA, an antisense oligo, an aptamer, or a decoy against CHRNB2.

(7) The molecular target therapeutic drug according to any one of (1) to (6), wherein a targeted disease of the molecular target therapeutic drug is stomach cancer, colorectal cancer, breast cancer, lung cancer, pancreatic cancer, or esophageal cancer.

(8) A monoclonal antibody produced by a hybridoma represented by Accession No. NITE P-02857.

(9) A hybridoma represented by Accession No. NITE P-02857.

(10) A test kit including: an antibody that recognizes CHRNB2 or a primer that quantifies mRNA expression of CHRNB2; and a reagent required for measurement.

(11) The test kit according to (10), wherein the antibody that recognizes CHRNB2 recognizes either WKPEEFDNMKKVRLPSKH (SEQ ID NO: 8) or TFLHSDHSAPSSK (SEQ ID NO: 9) of CHRNB2.

(12) The test kit according to (10), wherein the antibody that recognizes CHRNB2 is produced by a hybridoma represented by Accession No. NITE P-02857.

(13) The test kit according to (10), wherein the primer for quantifying mRNA expression of CHRNB2 is a primer represented by SEQ ID NOs: 1 and 2.

(14) A method of screening a molecular target drug that indexes binding of a test substance to a region exposed on a cell surface of CHRNB2.

(15) A method of screening a molecular target drug, the method comprising: culturing cells in the presence of a test substance; and indexing expression of CHRNB2.

(16) A molecular target therapeutic drug containing a substance that neutralizes or inhibits expression of Neuronal pentraxin receptor (NPTXR) as an active ingredient.

(17) The molecular target therapeutic drug according to (16), wherein the active ingredient is an antibody or a nucleic acid.

(18) The molecular target therapeutic drug according to (16) or (17), wherein the active ingredient recognizes either CESGLPRGLQGAGPRRDT (SEQ ID NO: 10) or KERVALSHSSRRQRQEVE (SEQ ID NO: 11) of NPTXR.

(19) The molecular target therapeutic drug according to (18), wherein the active ingredient is an antibody.

(20) The molecular target therapeutic drug according to (19), wherein the antibody is produced by a hybridoma represented by Accession No. NITE P-02856.

(21) The molecular target therapeutic drug according to (16) or (17), wherein the active ingredient is a siRNA, a miRNA, an antisense oligo, an aptamer, or a decoy against NPTXR.

(22) The molecular target therapeutic drug according to any one of (16) to (21), wherein a targeted disease of the molecular target therapeutic drug is stomach cancer, colorectal cancer, breast cancer, lung cancer, pancreatic cancer, or esophageal cancer.

(23) An antibody recognizing CESGLPRGLQGAGPRRDT (SEQ ID NO: 10) or KERVALSHSSRRQRQEVE (SEQ ID NO: 11) of NPTXR.

(24) A monoclonal antibody produced by a hybridoma represented by Accession No. NITE P-02856.

(25) A hybridoma represented by Accession No. NITE P-02856.

(26) An antibody recognizing an epitope represented by SEQ ID NO: 12 (GLPRGLQGAGPRRDT).

(27) A test kit including: an antibody that recognizes NPTXR or a primer that quantifies mRNA expression of NPTXR; and a reagent required for measurement.

(28) The test kit according to (27), wherein the antibody that recognizes NPTXR recognizes either CESGLPRGLQGAGPRRDT (SEQ ID NO: 10) or KERVALSHSSRRQRQEVE (SEQ ID NO: 11).

(29) The test kit according to (27), wherein the antibody that recognizes NPTXR is produced by a hybridoma represented by Accession No. NITE P-02856.

(30) The test kit according to (27), wherein the primer for quantifying mRNA expression of NPTXR is represented by SEQ ID NOs: 3 and 4.

(31) A method of screening a molecular target drug that indexes binding of a test substance to a region exposed on a cell surface of NPTXR.

(32) A method of screening a molecular target drug, the method comprising: culturing cells in the presence of a test substance; and indexing expression of NPTXR.

(33) A treatment method using the molecular target therapeutic drug according to (1) to (7).

(34) The treatment method according to (33) targeting a tumor with high CHRNB2 expression.

(35) The treatment method according to (34) including testing CHRNB2 expression by using the test kit according to (10) to (13).

(36) A treatment method using the molecular target therapeutic drug according to (16) to (22).

(37) The treatment method according to (36) targeting a tumor with high NPTXR expression.

(38) The treatment method according to (37) including testing NPTXR expression by using the test kit according to (27) to (30).

Advantageous Effects of Invention

Since the therapeutic drug according to the present invention is a therapeutic drug having a different action mechanism from anticancer agents used in the current treatment, it is expected to have the effect on a patient having no response to the conventional treatment.

DESCRIPTION OF EMBODIMENTS

Figure 1:
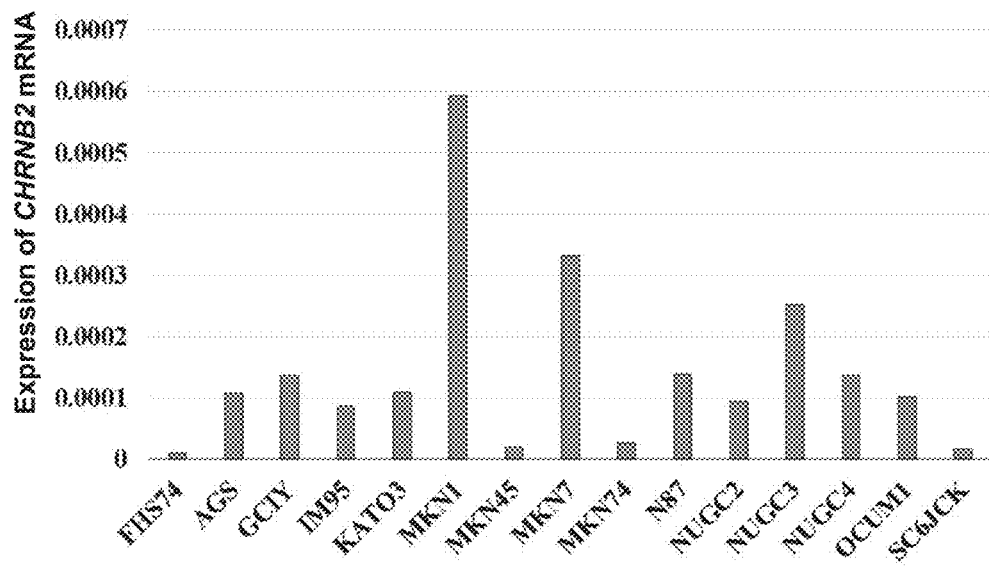
FIG. 1 is a diagram illustrating analysis of mRNA expression of CHRNB2 and NPTXR in stomach cancer cell lines.
Figure 1:
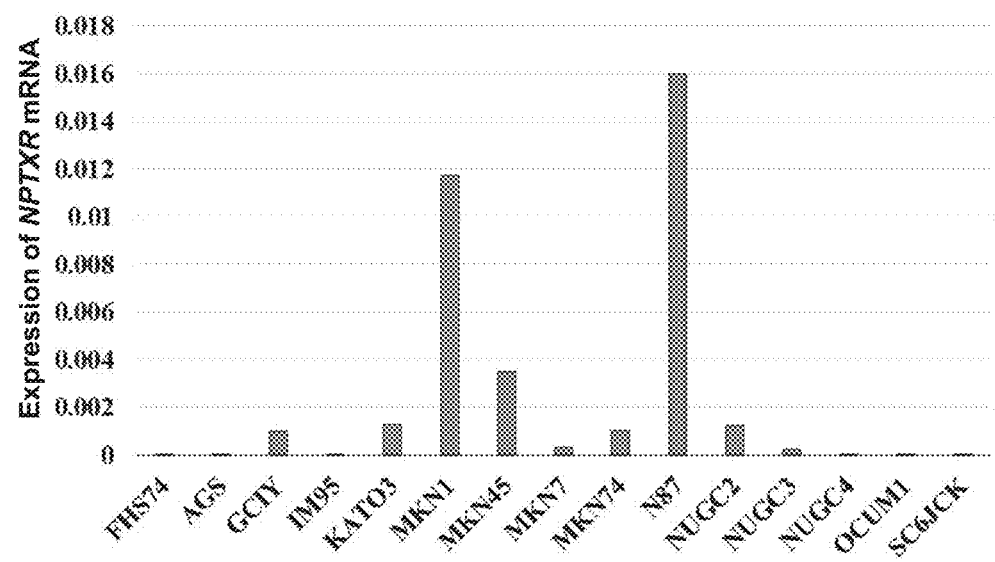

To identify a molecule involved in stomach cancer progression, the present inventors classified cases occurring after stomach resection in accordance with the progress and performed exhaustive expression analysis using a next-generation sequencer on mRNAs obtained from a stomach cancer primary lesion tissue. As a result, it was revealed that CHRNB2 and NPTXR that are receptor molecules are the molecules related to progression of stomach cancer.

According to a public database GeneCards, both CHRNB2 and NPTXR are genes with high expression in a nervous system organ such as a brain. CHRNB2 less expresses in other organs including a stomach, and no difference in the expression is found between the other organs. Further, although expression of NPTXR is found equally in organs other than the nervous system, no difference in expression is found between organs. Further, although a result that implies involvement of NPTX/NPTXR in a neuroblastoma was reported for the function of these genes (non-Patent Literature 3), a relation to a tumor of a stomach cancer or the like or the role in a tumor has not been reported for CHRNB2 and thus is unknown. Further, also for the NPTXR, although there has been a report for a neuroblastoma as described above, there has been no report for other cancer types, and the role in an epithelial tumor is also unknown.

As a result of analysis made by the present inventors, a relation between these receptor molecules and tumor development and an action in a tumor were revealed. Further, proliferation inhibition of tumor cells and antitumor activity were observed in a neutralizing antibody that neutralizes these molecules or a nucleic acid that inhibits expression of these molecules. Therefore, a substance that inhibits the function of CHRNB2 and NPTXR proteins or inhibits a gene expression functions as a molecular target therapeutic drug.

As described below, in the Examples, an antibody or a siRNA is used as a substance that neutralizes or inhibits expression of CHRNB2 and NPTXR. However, not only such an antibody and siRNA but also any substance may be used as long as it is a substance that neutralizes or inhibits expression of CHRNB2 and NPTXR.

Further, since proliferation inhibition and antitumor activity on tumor cells were observed in the substance that neutralizes or inhibits expression of CHRNB2 or NPTXR, it is possible to screen a therapeutic drug targeting CHRNB2 or NPTXR.

Specifically, the binding to a region exposed on the cell surface of CHRNB2 or NPTXR may be evaluated. The region exposed on the cell surface of CHRNB2 or NPTXR can be predicted by using a program of analyzing the conformation of a protein. For example, since peptides represented by SEQ ID NOs: 8 to 11 are considered to be exposed on the cell surface, screening can be made by evaluating the binding to these peptides.

Further, since the effect is observed in a substance that inhibits expression of CHRNB2 or NPTXR, the expression of CHRNB2 or NPTXR may be used as an index to screen molecular target drugs. Specifically, cells expressing CHRNB2 or NPTXR are cultured in the presence of a candidate substance, the mRNA or the protein of CHRNB2 or NPTXR is quantified, and the effect of the candidate substance can be examined. A known method can be used for measuring gene expression and protein expression, it is possible to determine gene expression by RT-PCR and determine protein expression by ELISA or the like, for example.

In the present invention, an anti-CHRNB2 antibody and an anti-NPTXR antibody mean an immune globulin molecule binding to CHRNB2 or NPTXR. Furthermore, as illustrated below, the present inventors have already acquired not only polyclonal antibodies to CHRNB2 and NPTXR but also monoclonal antibodies thereto. The antibodies of the present invention also include a human chimera antibody, a humanized antibody made as a humanized CDR grafted antibody, and a human antibody using a genetically modified mouse obtained from these monoclonal antibodies by using a gene recombination technology. Humanized antibodies and human antibodies have less side effect than antibodies of animals other than human when administered to a human, and the therapeutic effect persists for a long time. Further, the scope of the present invention includes antibody fragments such as Fab, Fab', (Fab')$_2$, and Fv fragments, a linear antibody, single-strand Fv(scFv), a bispecific antibody, or the like.

Furthermore, epitope analysis is also performed on an anti-NPTXR monoclonal antibody. The term "epitope" refers to a part of an antigen recognized by an antibody and means a site on an antigen to which a domain including antibody variable region disclosed in the present specification binds. When a polypeptide such as NPTXR is used as an antigen, the antibody may recognize a linear amino acid sequence or may recognize a three-dimensional conformation, and an epitope can be defined by the amino acid sequence or the antigen structure. Since it is considered that antibodies binding to the same epitope have the same characteristic feature, an anti-NPTXR monoclonal antibody can be defined by an epitope sequence.

Further, a nucleic acid medicine may be not only a siRNA demonstrated in the following examples but also any medicine that inhibits expression of CHRNB2 or NPTXR genes and includes a medicine that inhibits mRNA expression, such as a miRNA or an antisense oligo without being limited to the siRNA. Further, a nucleic acid that binds to a CHRNB2 or NPTXR protein as with an antibody, such as an aptamer, a decoy, or the like and neutralizes the activity thereof is included.

Furthermore, an agent that inhibits a signal cascade located in the downstream of CHRNB2 or NPTXR receptors and thereby disables the signal from these receptors may be used. For example, the existence of a PI3K/Akt signal pathway was identified as the downstream signaling pathway of NPTXR, as demonstrated below. Therefore, in treatment of a tumor with high NPTXR expression, the effect may be enhanced when a PI3K/Akt inhibitor is used alone or used in combination with a molecular target therapeutic drug that neutralizes or inhibits expression of NPTXR.

Further, when a molecular target therapeutic drug that neutralizes or inhibits expression of CHRNB2 or NPTXR is administered, it is necessary to examine CHRNB2 or NPTXR expression in advance in order to avoid unnecessary treatment. Expression of CHRNB2 or NPTXR can be examined by PCR or immunohistochemical staining with an antibody, as demonstrated below. A primer set used in PCR or an antibody used for determining expression and a reagent required for determination may be combined to make a test kit. Since expression of CHRNB2 or NPTXR is deeply correlated to prognosis, such a test kit can be used to perform prognosis forecast.

Although data demonstrated below was obtained from analysis of stomach cancer, a molecular target therapeutic drug targeting CHRNB2 or NPTXR can be applied not only to stomach cancer but also to various cancer types that express CHRNB2 or NPTXR at a high level or a disease that expresses CHRNB2 or NPTXR excessively.

According to a cancer genome database, TCGA (The Cancer Genome Atlas), the expression of CHRNB2 in acute myelogenous leukemia, breast cancer, bile duct cancer, glioblastoma, glioma, lung cancer, malignant melanoma, malignant mesothelioma, pancreatic cancer, uterine cancer, uterine sarcoma, uveal melanoma, and renal cell cancer is higher than or equal to that in stomach cancer. Since, the expression of CHRNB2 is high even with a normal tissue in the cranial nervous system, it is considered that the high expression of CHRNB2 in glioblastoma and glioma reflects expression of the original tissue. However, the expression of CHRNB2 in the original organ in acute myelogenous leukemia, breast cancer, bile duct cancer, lung cancer, malignant melanoma, malignant mesothelioma, pancreatic cancer, uterine cancer, uterine sarcoma, and renal cell cancer is equal to or less than that in stomach. Therefore, the high expression of CHRNB2 in these cancer types is certainly correlated to carcinogenesis. Further, as demonstrated in the following examples, since proliferation of cancer cells is inhibited by neutralizing or inhibiting the expression of CHRNB2, a medicine targeting CHRNB2 is certainly to have the effect on these cancer types.

Further, the expression of NPTXR in bladder cancer, breast cancer, esophageal cancer, glioblastoma, glioma, lung cancer, malignant melanoma, ovarian cancer, malignant pheochromocytoma, prostatic cancer, testicular germ cell tumor, thyroid cancer, pancreatic cancer, uterine cancer, and renal cell cancer is higher than or equal to that in stomach cancer. Therefore, also in these cancer types, a medicine targeting NPTXR is certainly to have the effect on these cancer types in the same manner as in stomach cancer.

Further, although an antibody or a nucleic acid targeting CHRNB2 or NPTXR is used alone in the Examples demonstrated below, such an antibody or a nucleic acid can be used in combination. The inventors have found two regions that can be targeted by anti-CHRNB2 antibodies or anti-NPTXR antibodies, respectively. Therefore, these two types of antibodies against CHRNB2 or NPTXR may be used at the same time, or antibodies against the two molecules, CHRNB2 and NPTXR, may be used in combination. Further, it is possible to use these antibodies in combination with a chemotherapeutic agent or a target medicine such as trastuzumab, ramucirumab, nivolumab, or the like that have already been approved.

Description will be provided below with reference to data.

1. Identification of CHRNB2 and NPTXR

<Identification of a Molecule Involved in Stomach Cancer Progression that can be a Target Molecule>

In Nagoya University, Faculty of Medicine, case histories in which curative resection was performed on stage III stomach cancer and internal use of S-1 was applied as post-operative adjuvant therapy have been grouped so far in accordance with the progress. Stomach cancer patients can be broadly categorized into a long-term recurrence-free group and a recurrence metastasis group. An over-five-year long-term recurrence-free group means "stomach cancer that might be controlled by the current treatment", and this was used as a control and compared with the recurrence metastasis group. Further, since metastasis includes different types of metastasis such as peritoneal dissemination, liver metastasis, and lymph node metastasis, the recurrence metastasis group was categorized into a peritoneal dissemination recurrence group, a liver metastasis recurrence group, and a lymph node metastasis recurrence group, and expression profiling was performed by transcriptome analysis on RNAs obtained from each four stomach cancer primary lesion tissues for four groups including the above recurrence metastasis groups and the over-five-year long-term recurrence-free group.

For surgery samples, RNAs were extracted by using RNeasy kit (by QIAGEN). For the extracted total RNA, the library for sequencing was prepared in accordance with a standard protocol by using TruSeq RNA Sample Prep Kit (By illumina).

Next, Paired-End sequencing was performed by using a next-generation sequencer Hiseq (by illumina), and transcriptome analysis was performed. Data was acquired with a read base length of 100 bases/read, a reference acquisition read number of 100 million read pairs (200 million reads)/lane, and a reference acquisition data level of 20 Gb/lane.

Analysis was conducted by performing a mapping process to a designated reference sequence by using HiSeq software, calculating the expression level of each gene based on a Fragments per kilobase of exon per million mapped sequence reads (FPKM) value, and creating an inter-subject comparison table.

The expression level of 57749 molecules was analyzed exhaustively by transcriptome analysis, the over-five-year long-term recurrence-free group and the other three groups were compared with each other, and detection of a molecule which expressed at a high level in the recurrence metastasis group was performed. Analysis was performed by focusing on two points that expression increases in all the metastatic forms and that the molecule is a receptor molecule can be premised on an approach as an antibody medicine considering a roadmap to inhibitor development. As a result, CHRNB2 and NPTXR were selected as candidate molecules that meet criteria.

TABLE 1

| gene | Group | | | | | |
|---|---|---|---|---|---|---|
| | peritoneal dissemination recurrence group | | liver metastasis recurrence group | | lymph node metastasis recurrence group | |
| | $\log_2$ | p-value | $\log_2$ | p-value | $\log_2$ | p-value |
| CHRNB2 | 2.45 | 0.0001 | 4.88 | 0.0001 | 6.36 | <0.0001 |
| NPTXR | 4.39 | <0.0001 | 2.26 | 0.0017 | 1.71 | 0.0183 |

As indicated in Table 1, CHRNB2 and NPTXR significantly express at a high level in all the recurrence groups compared to the over-five-year long term recurrence-free group that is the control. Although the roles of both the molecules of CHRNB2 and NPTXR in a malignant tumor were unclear, further research was conducted since these molecules are receptor proteins and may be a target for drug discovery having a mechanism that is completely different from that of the existing molecular targeted drug for stomach cancer.

<Quantitative Analysis of mRNA Expression Level of CHRNB2 and NPTXR in Stomach Cancer Cell Lines>

The mRNA expression levels of CHRNB2 and NPTXR were quantified by quantitative PCR using 14 types of stomach cancer cell lines and FHS74 that is a non-neoplastic glandular ductal epithelial cell line (FIG. 1). The RNA was extracted and purified by RNeasy kit (by QIAGEN), and the quantitative PCR was performed using ABI STEPOnePlus Real-Time PCR System (by Applied Biosystems) by heating at 95° C. for 10 minutes followed by 40 cycles of 95° C. for 10 seconds and 60° C. for 30 seconds of PCR amplification cycles. Note that glyceraldehyde-3-phosphate dehydrogenase (GAPDH) was used as a control to normalize the value of each RNA. The sequences of the used PCR primers were as follows.

```
[CHRNB2]
                                  (SEQ ID NO: 1)
Forward:          AGCGAGGACGATGACCAG (SEQ ID NO: 2)
Reverse:          GGTGCCAAAGACACAGACAA

[NPTXR]
                                  (SEQ ID NO: 3)
Forward:          TCATTCTGGAGCTGGAGGAC (SEQ ID NO: 4)
Reverse:          GGCAGCTGAGAGGTTCACA

[Control GAPDH]
                                  (SEQ ID NO: 5)
Forward:          GAAGGTGAAGGTCGGAGTC (SEQ ID NO: 6)
Reverse:          GAAGATGGTGATGGGATTTC (SEQ ID NO: 7)
Probe:            CAAGCTTCCCGTTCTCAGCC
```

In FHS74 that is non-neoplastic glandular ductal epithelial cell line, both the expression levels of molecules of CHRNB2 and NPTXR were significantly low. In contrast, out of 14 types of stomach cancer cell lines, an increase in expression was observed in 11 cell lines (79%) for CHRNB2 and in 9 cell lines (64%) for NPTXR. That is, it was found that an increase in expression of CHRNB2 and NPTXR was observed in stomach cancer tissues of the patients of the recurrence metastasis group and stomach cancer cell lines.

2. Functional Analysis of CHRNB2 and NPTXR Using Cell Lines
<Analysis Result Using Knockout Cell Lines>
(1) Functional Analysis Using CHRNB2 Knockout Cell Lines MKN1 known as high malignant stomach cancer cell line was used to prepare knockout (KO) cells of CHRNB2 by genome editing by using CRISPR-CAS9 method (Gene Art Platinum Cas9 nuclease; by Thermo Fisher Scientific). Knockout cells were selected by single cell cloning, and the selected knockout cells were confirmed by a direct sequencing method or a Western blotting method. Comparison with the control cells (untreated MKN1) was made for the proliferative ability, the apoptotic ratio, the migratory ability, the invasive ability, and the adhesion ability (FIG. 2).

Figure 2A:
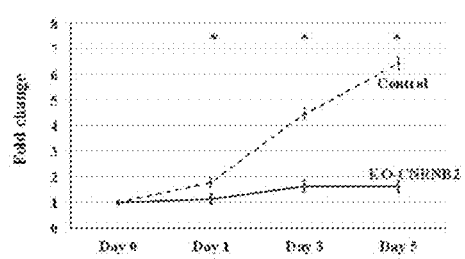
FIG. 2 shows diagrams of functional analysis of CHRNB2 using CHRNB2 knockout cells. (A) shows an analysis result of the cell proliferative ability, (B) shows an analysis result of the apoptotic ratio, (C) shows an analysis result of the migratory ability, (D) shows an analysis result of the invasive ability, and (E) shows an analysis result of the adhesion ability.

The proliferative ability of cells was analyzed by the following method. The cells were seeded in a 96-well plate so that $1\times10^4$ cells were each placed thereon, and the cell proliferation was determined over time up to the fifth day in a DMEM medium added with 2% fetal bovine serum. In the measurement, 10 μL Cell Counting Kit-8 (by Dojindo Molecular Technologies) was added and measure the absorbance, and the absorbance was displayed with the value at the start of determination being defined as 1 (FIG. 2A). In the CHRNB2 knocked-out MKN1 cells (KO-CHRNB2 cell), the cell proliferation rate decreased, and a significant difference in the number of cells was observed from one day after seeding (indicated by * in the drawing; hereafter, the same indication applies to those with a significant difference observed). Further, for KO-CHRNB2 cells, substantially no proliferation was found even on the fifth day from seeding. Note that a significant difference was analyzed by Mann-Whitney assay.

The apoptotic cell ratio was analyzed as follows. Annexin V staining was performed by using Annexin V Alexa Fluor 568 conjugate (by Thermo Fisher Scientific). Ten μL Annexin V reagent was added to $1\times10^6$ cells, which were placed on a slide and let stand at the room temperature for 15 minutes, then the number of cells and the number of Annexin V positive cells were counted using a fluorescence microscope (FSX100, by Olympus).

Figure 2B:
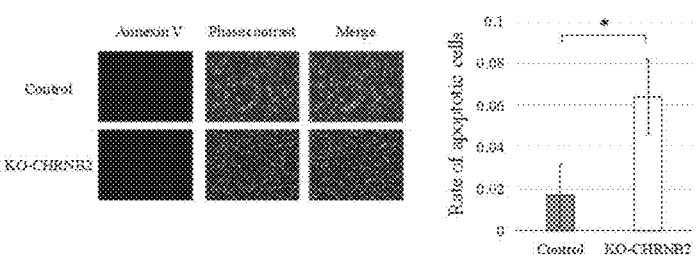

In KO-CHRNB2 cells, the apoptotic ratio increased significantly (FIG. 2B). As shown in FIG. 2A, the cell proliferative ability notably decreased in CHRNB2 knockout compared to the stomach cancer cell line MKN1 that is parent cell line. This result revealed that one of the mechanisms that inhibited proliferation of KO-CHRNB2 cells was apoptosis induction. That is, it is considered that apoptosis is less likely to be induced due to excessive expression of CHRNB2 and therefore malignancy becomes high.

Figure 2C:
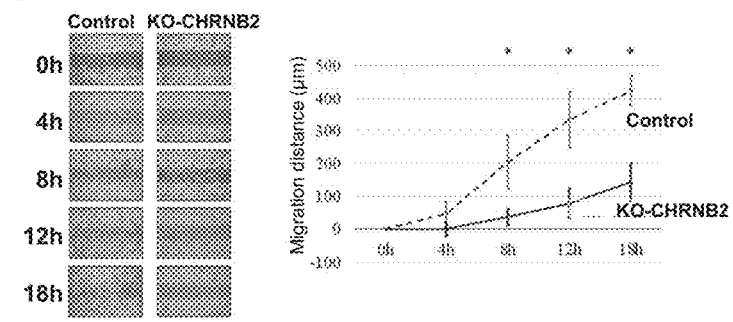

The migratory ability of cells was evaluated by wound-healing assay. In a 12-well plate, $2\times10^4$ cells were seeded respectively and forming a wound gap at a predetermined width by ibidi Culture insert method (by ibidi), and the seeded cells were cultured in a serum-free medium. The insert was removed after 24 hours from the seeding, and the wound width was measured at 200 μm interval every 6 hours. In the measurement, 10 positions in each well were measured by using a microscope of 40 times magnification and obtained the mean and the standard deviation (FIG. 2C). It was revealed that, knockout of CHRNB2 also significantly reduced the migratory ability.

Figure 2D:
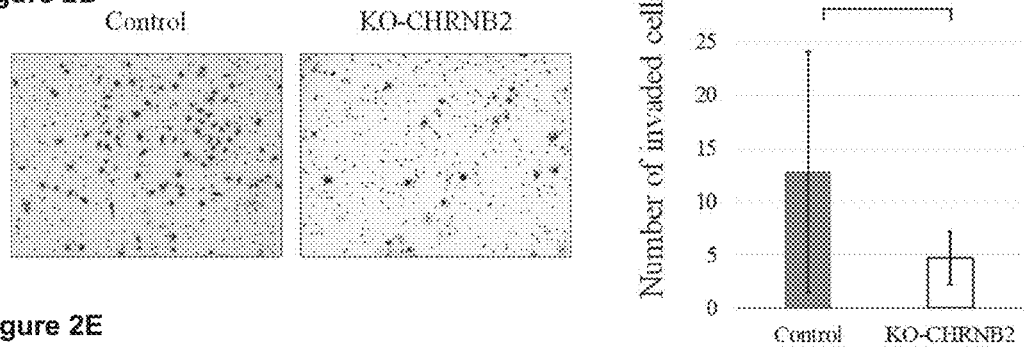

The invasive ability of the control cells and KO-CHRNB2 cells was evaluated by Matrigel invasion assay. The assay was performed in accordance with a protocol by using BioCoat Matrigel invasion Chambers (by BD Biosciences). Specifically, $2.5\times10^4$ cells were seeded in 1 well respectively, and after culture in a serum-free DMEM medium for 24 hours, the cells on a membrane bottom surface were fixed, stained by DiffQuick (by Sysmex), and observed under a microscope to count the number of cells. The microscope observation was performed at a magnification of 200 times, and the mean and the standard deviation were obtained of randomly selected five fields. Knockout of CHRNB2 also reduced the invasive ability significantly (FIG. 2D).

Figure 2E:
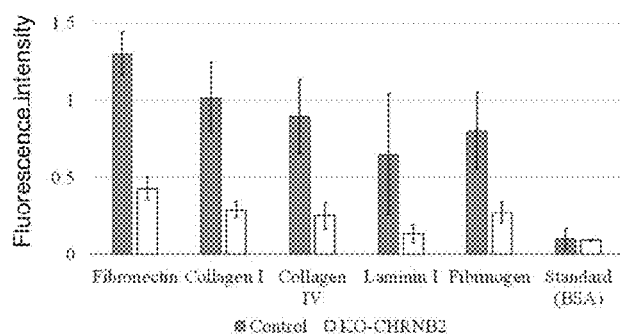
Figure 3A:
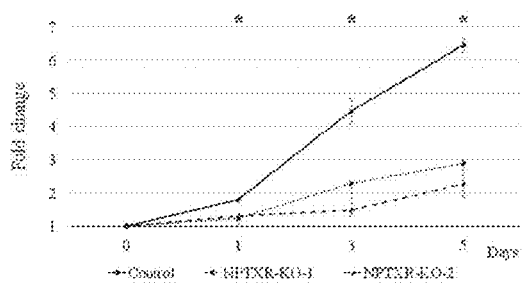
FIG. 3 shows diagrams of functional analysis of NPTXR using NPTXR knockout cells. (A) shows an analysis result of the cell proliferative ability, (B) shows an analysis result of the apoptotic ratio, (C) shows an analysis result of the migratory ability, (D) shows an analysis result of the invasive ability, and (E) shows an analysis result of the adhesion ability.
Figure 3B:
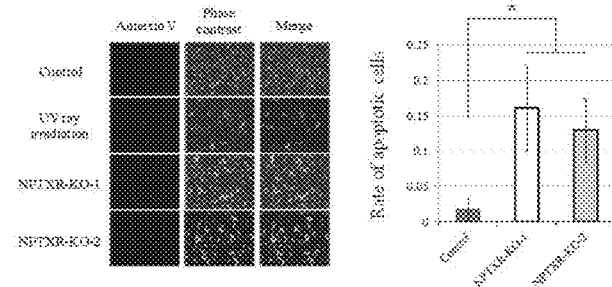
Figure 3C:
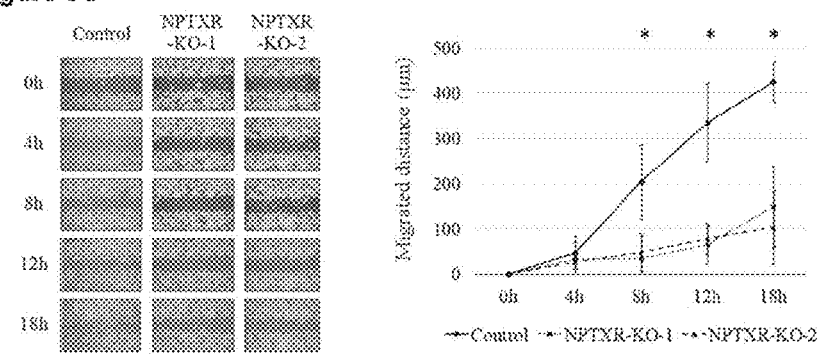
Figure 3D:
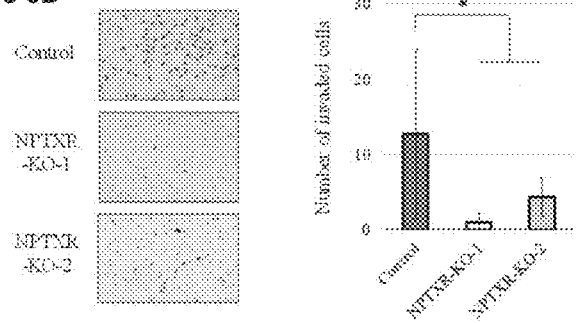
Figure 3E:
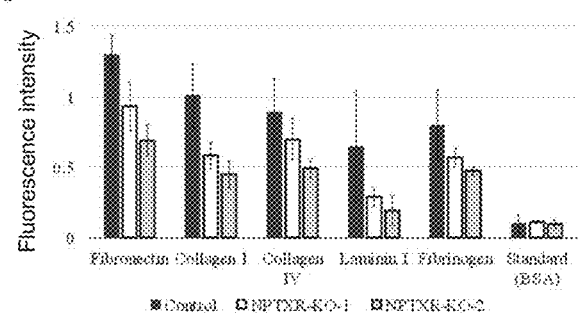

The cell adhesion ability was analyzed as follows by using CytoSelect 48-Well Cell Adhesion Assay (by Cell Biolabs). On a plate coated with an adhesion factor, $7.5\times10^4$ cells were seeded per 1 well respectively, and each absorbance was determined after one hour culture in a serum-free DMEM medium. The adhesion abilities to five types of cell adhesion factors were analyzed, which revealed that the adhesion ability was also reduced in KO-CHRNB2 cells (FIG. 2E).

The above results revealed that, when expression of CHRNB2 is lost in the MKN1 cells, the characteristic features related to cancer progression, such as the proliferative ability, the apoptotic ratio, the migratory ability, the invasive ability, and the adhesion ability changed notably. Therefore, by inhibiting CHRNB2 function, it may be possible to inhibit cancer progression of stomach cancer.

(2) Functional Analysis Using NPTXR Knockout Cell Lines

Next, for NPTXR, similarly, knockout cells were prepared by using a CRISPR-CAS9 method with stomach cancer cell line MKN1, and the proliferative ability, the apoptotic ratio, the migratory ability, the invasive ability, and the adhesion ability were analyzed (FIG. 3).

As shown in FIG. 3, in NPTXR knocked-out cells (NPTXR-KO-1, NPTXR-KO-2 cells), the proliferative ability, the migratory ability, the invasive ability, and the adhesion ability were all reduced significantly compared to cells of parental cell line, MKN1, and the apoptotic ratio was increased significantly. The results from two knockout cell lines that were independently established that the proliferative ability, the migratory ability, the invasive ability, and the adhesion ability were reduced significantly compared to cells of parental cell line, MKN1, and the apoptotic ratio was increased significantly. Therefore, as with CHRNB2, it was revealed that, when NPTXR is lost in the stomach cancer cell MKN1, the characteristic features related to cancer progression were notably lost.

The above result implied that NPTXR expression affected apoptosis and accelerated cell proliferation. Accordingly, NPTXR knockout cell lines were used to analyze the characteristic features associated with apoptosis. It is known that a mitochondrion is deeply related to apoptosis. It is known that a loss of a membrane potential of a mitochondrion facilitates release of cytochrome c, activation of caspase cascade, and apoptosis is induced. Accordingly, it was analyzed whether or not NPTXR expression is involved in apoptosis via a mitochondrion (FIG. 4).

Figure 4A:
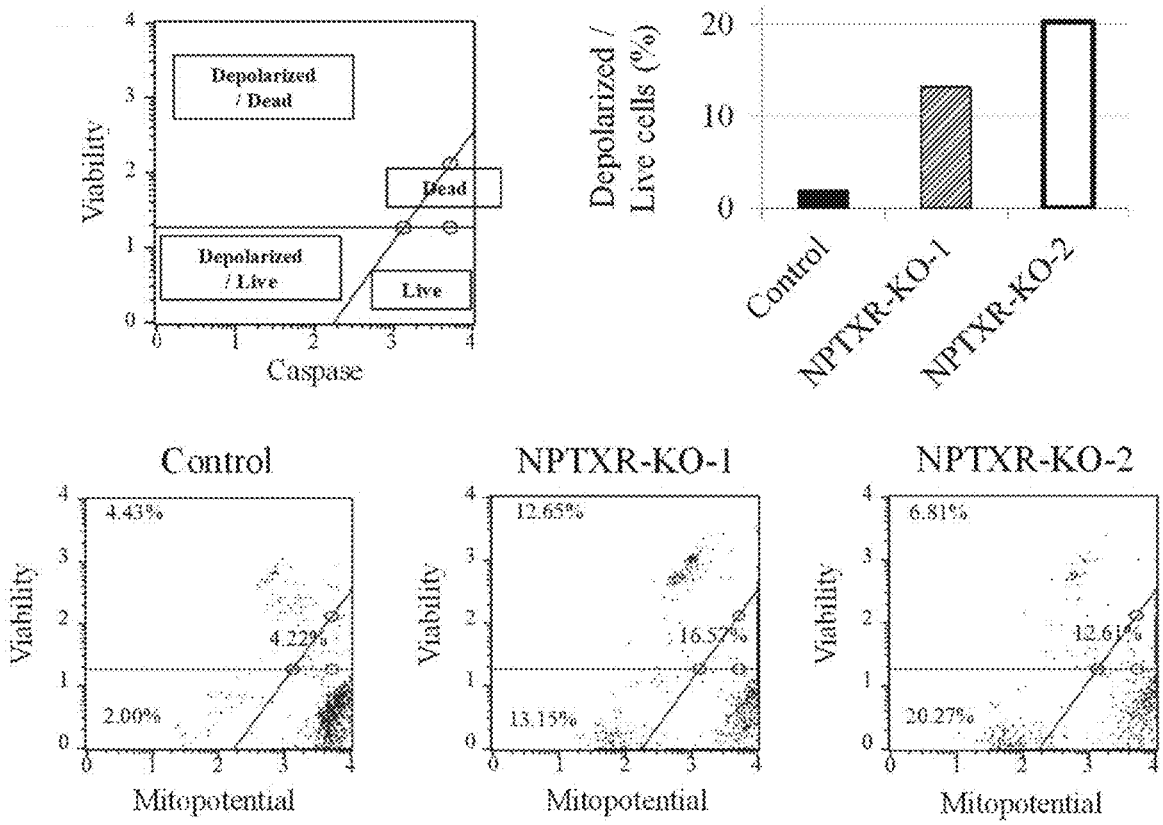
FIG. 4 shows diagrams indicating analysis results of influence on an apoptotic pathway by NPTXR expression. (A) is a diagram illustrating depolarization of mitochondria, and (B) is a diagram illustrating an analysis result of caspase activity. (C) is a diagram illustrating an analysis result of activities of major caspase family molecules.
Figure 4B:
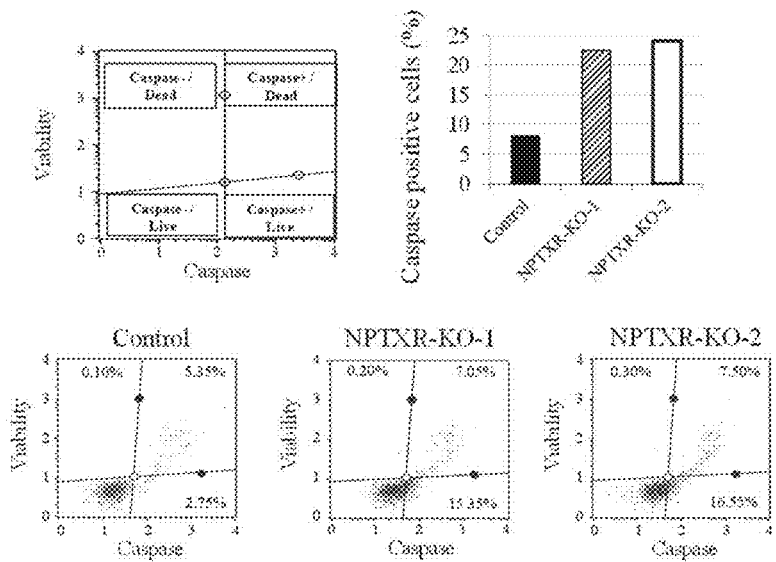

First, the membrane potential of a mitochondrion was visualized, a living cell in which mitochondrial depolarization occurred, that is, a cell in which apoptosis was induced was visualized (FIG. 4(A)). Each $1\times10^5$ cells of NPTXR-KO-1 and NPTXR-KO-2 that are the NPTXR knockout cells and MKN1 cells that are parental cells as a control were stained by Muse MitoPotential kit (by Merck Millipore) and analyzed by a cell sorter.

In both the two cell lines in which NPTXR was knocked out, the ratio of living cells in which depolarization occurred increased by around 6.5 to 10 times compared to the MKN1 cells that are parental cells. The mitochondrial depolarization indicates that apoptosis induced via mitochondria. The above results indicate that NPTXR expression inhibits apoptosis induced via mitochondria.

Next, in NPTXR knockout cells, activity of a caspase that is a protease that causes progress of apoptosis was analyzed. Each $1\times10^5$ cells of cell lines were stained respectively by Muse MitoPotential kit (by Merck Millipore) and analyzed by a cell sorter. It was observed that, in all the knockout cell lines, caspase positive cells (Caspase+/Dead and Caspase+/Live subsets) increased. That is, it is considered that NPTXR expression inhibits caspase activity and inhibits apoptosis.

Figure 4C:
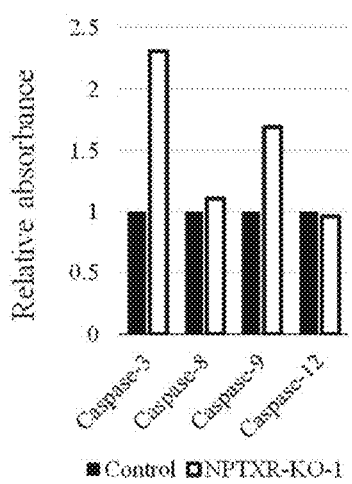

Next, it was analyzed which caspase in the caspase family is activated by using Caspase Colorimetric Assay Kit (by BioVision) (FIG. 4(C)). In caspases, there are an initiator caspase responsible for the initial phase of apoptosis induction and an effector caspase responsible for apoptosis execution. The caspase 3 is an effector caspase, and the caspases 8 and 9 are initiator caspases. It is considered that the caspase 12 works as an initiator that is a caspase found only in mice and may induce apoptosis due to endoplasmic reticulum stress.

It was found that the caspase 3 that is an effector caspase and the caspase 9 that is an initiator caspase are activated by knockout of NPTXR expression. The above results indicated that apoptosis induction on a mitochondrial pathway was inhibited by the NPTXR expression, and as a result, caspase activation was also inhibited.

Figure 5A:
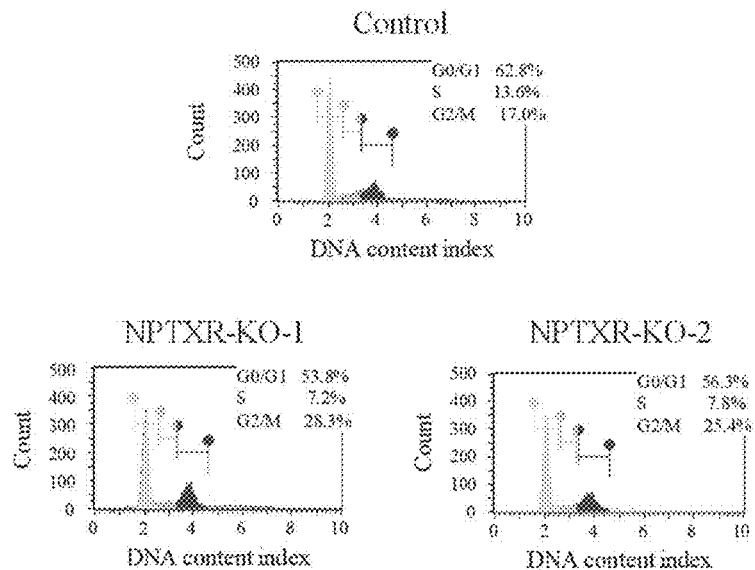
FIG. 5 is a diagram of analysis of effect of NPTXR expression on the cell cycle. (A) is a diagram illustrating an analysis result obtained by a cell sorter, and (B) is a diagram illustrating an analysis result obtained by microscopic observation.
Figure 5B:
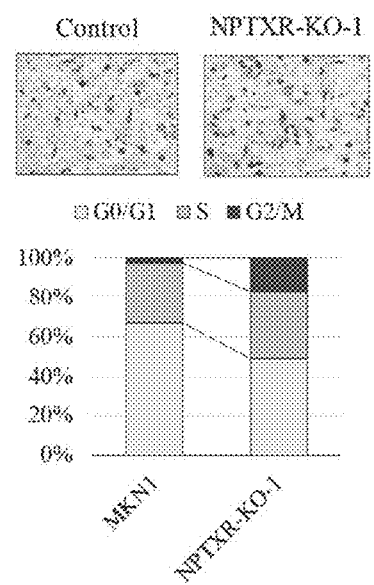

Next, characteristics related to cell proliferation were analyzed. First, effect of NPTXR expression on the cell cycle was analyzed. Analysis was performed using Muse Cell Cycle kit (by Merck Millipore) by a cell sorter (FIG. 5(A)), or analysis was performed using Cell Cycle Assay Cell-Clock Kit (by Biocolor) by counting the number of cells at each cell cycle under a microscope in eight fields (FIG. 5(B)). In both the analysis, a cell cycle arrest occurred in a G2/M phase in the NPTXR knockout cell lines, it was indicated that NPTXR expression is involved also in the cell cycle.

Figure 6:
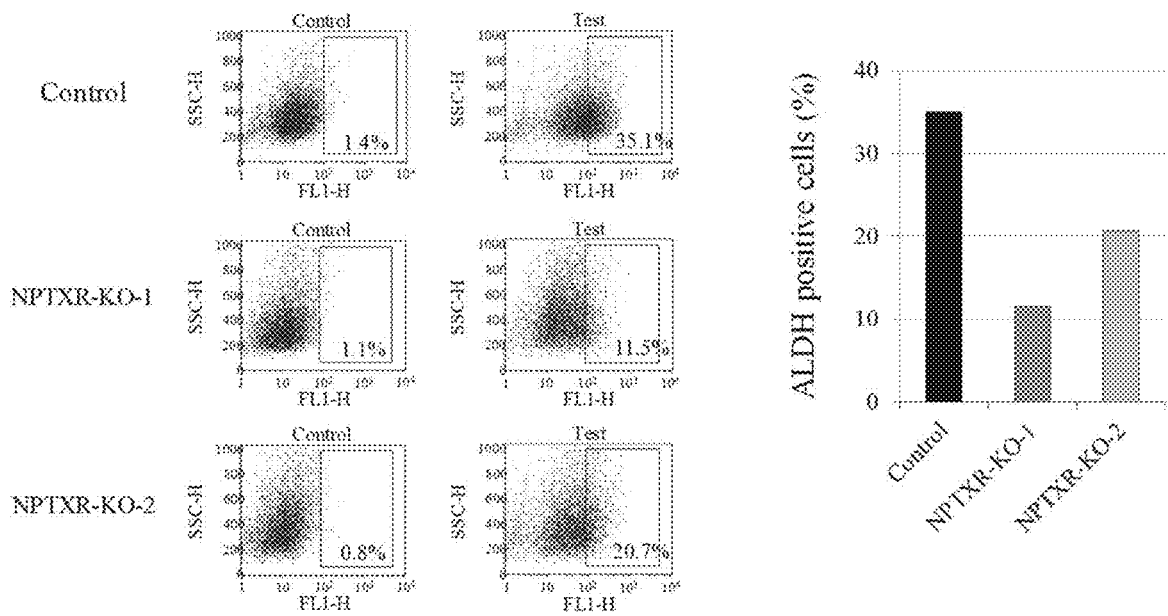
FIG. 6 is a diagram illustrating an analysis result of effect of NPTXR expression on the cancer stemness.

Cancer cells have characteristics of having a high proliferation ability, a resistance against apoptosis, and an invasion and metastasis ability as shown above. The cancer stem sell hypothesis has been proposed that not all the cancer cells have similar properties, but some of the cancer cells have properties of a stem cell, and a cancer develops. Activity of Aldehyde Dehydrogenase (ALDH) expressing in stem cells was used as an index to analyze the ratio of the stem cells. The ratio of ALDH positive cells was determined by ALDEFLOUR fluorescent reagent system (by Stem Cell Technologies) (FIG. 6). Each $1\times10^5$ cells of MKN1 cells, which are cells of parental cell line, and of NPTXR knockout cells were stained and analyzed, respectively.

Comparison between the value of cells before treatment (control) and after treatment of a reagent (test) indicated that, in the NPTXR knockout cells, the ALDH positive cells decreased compared to MKN1 cells that are parental cells. That is, it was indicated that the NPTXR expression also affected the stem cell property.

Next, the proliferative property of cancer cells was analyzed (FIG. 7). It is known that PI3 kinase (PI3K) is an intracellular signal transduction system, regulates a variety of functions such as Akt-mediated survival, proliferation, protein synthesis, Rac-mediated cell mobility, and is deeply involved in cancer, and it expresses at a high level in various cancers.

Figure 7A:
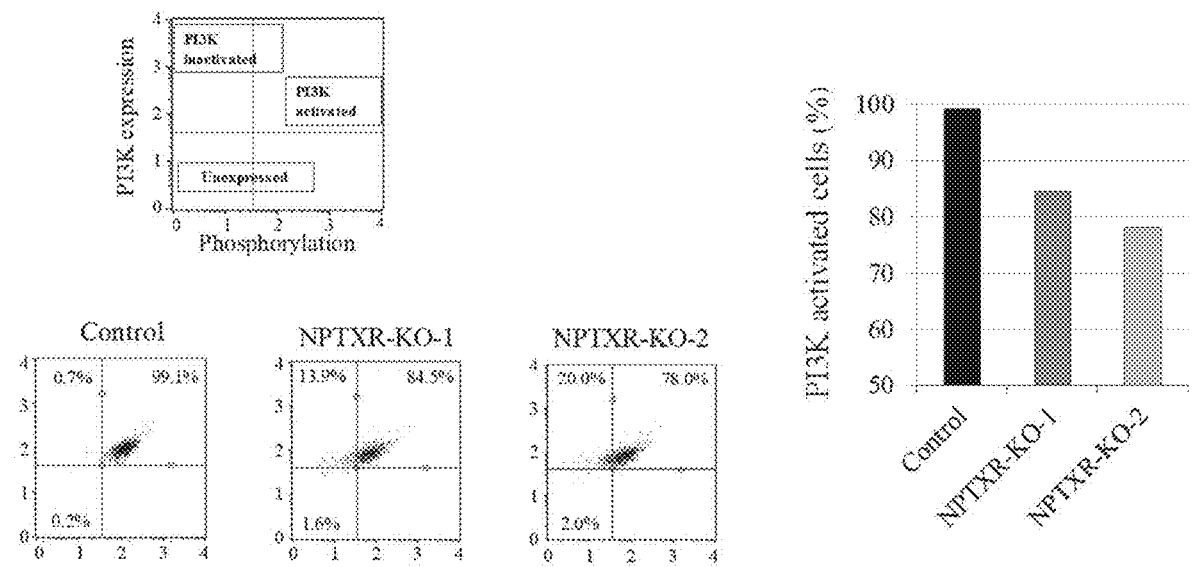
FIG. 7 is diagram illustrating analysis results of effect of NPTXR expression on cell proliferation. (A) is a diagram illustrating an analysis result of a PI3K pathway that affects proliferation of cancer cells. (B) is a diagram illustrating an analysis result of the sensitivity to an anticancer agent 5-FU.

The activity of PI3K in the NPTXR knockout cells was determined by using Muse PI3K Activation Dual Detection Kit (by Millipore) (FIG. 7(A)). While PI3K was activated in most cells in MKN1 cells that are parental cells, a reduction in the ratio of PI3K positive cells was observed in the NPTXR knockout cells. It was indicated that the PI3K activity was inhibited by a loss of NPTXR expression.

Figure 7B:
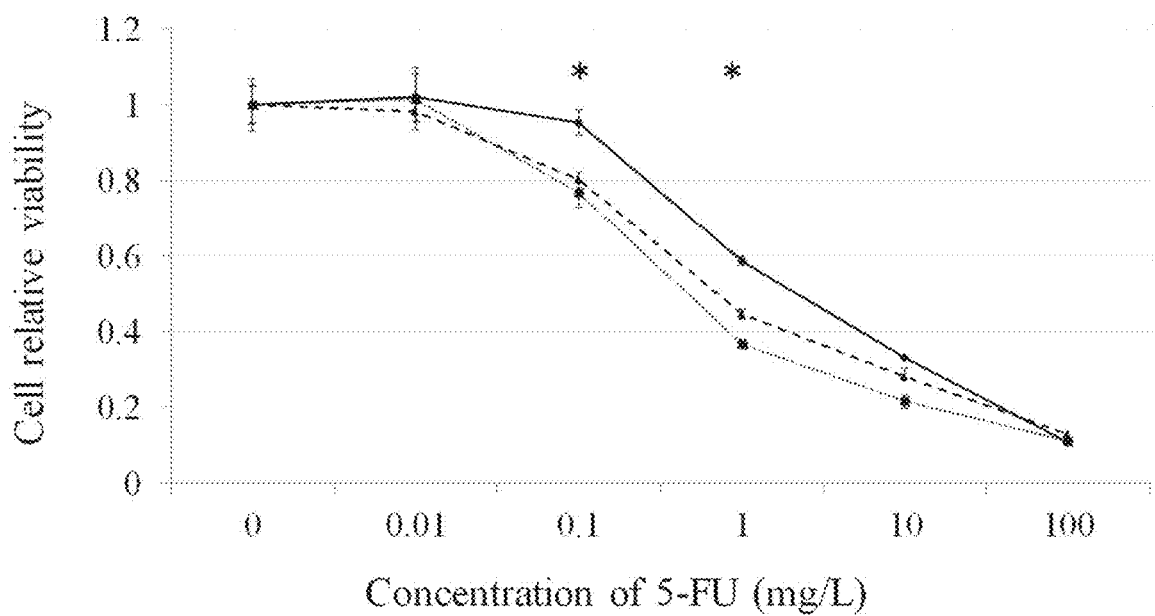

Furthermore, it was analyzed whether or not NPTXR expression affects the sensitivity to 5-FU that is an anticancer agent commonly used for stomach cancer (FIG. 7(B)). MKN1 cells that are parental cells as a control, NPTXR-KO-1 cells, and NPTXR-KO-2 cells were seeded in a well by $5\times10^3$ cells, respectively, and exposed to 0, 0.01, 0.1, 1, 10, and 100 mg/L 5-FU, and the number of cells was determined by Cell Counting Kit-8 after 72 hours.

In all the NPTXR knockout cells, the sensitivity to 5-FU was increased. In particular, a significant difference in sensitivity was observed in the low concentration region such as 0.1 and 1 mg/L compared to the parent cells, MKN1.

This result means that inhibition of NPTXR expression increases the sensitivity to 5-FU and implies a possibility that a higher effect may be obtained by a combined use of an NPTXR expression inhibitor and 5-FU.

(3) Analysis Using Mouse Subcutaneous Tumor Models

CHRNB2 or NPTXR knocked-out MKN1 cells and untreated MKN1 cells were implanted by $1\times10^6$ cells subcutaneously in both shoulders of 9-week old nude mice (BALB c nu/nu, obtained from Japan SLC), and the tumor volume was determined over time. Note that three mice were used for each group, the tumor volume was measured and calculated by shorter diameter×shorter diameter×longer diameter/2.

Figure 8A:
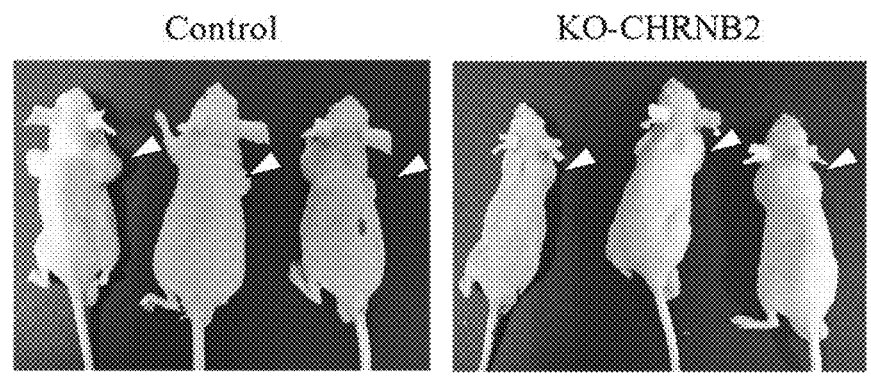
FIG. 8(A) is a diagram illustrating an analysis result of the tumorigenic ability of CHRNB2 knockout cells in a mouse subcutaneous tumor model.
Figure 8A:
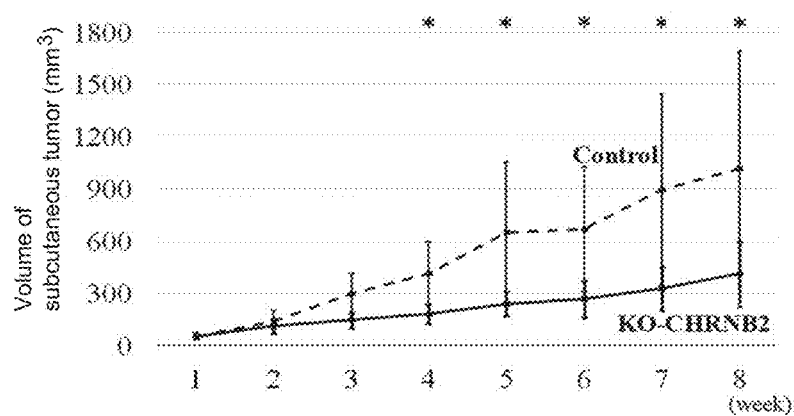
Figure 8B:
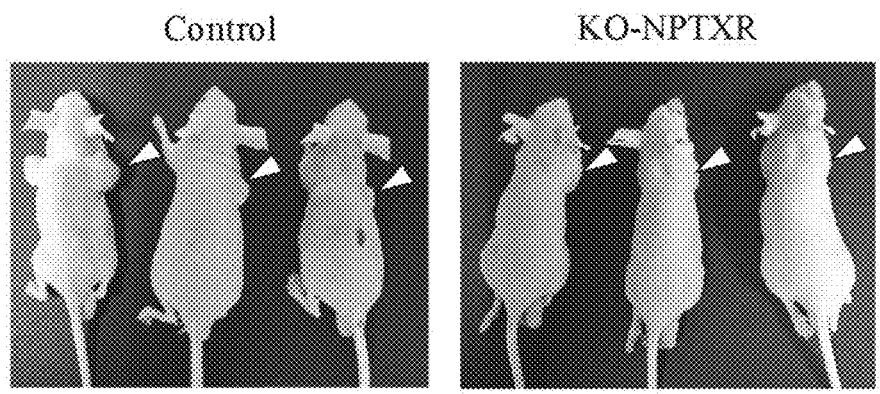
FIG. 8(B) is a diagram illustrating an analysis result of the tumorigenic ability of NPTXR knockout cells in a mouse subcutaneous tumor model.
Figure 8B:
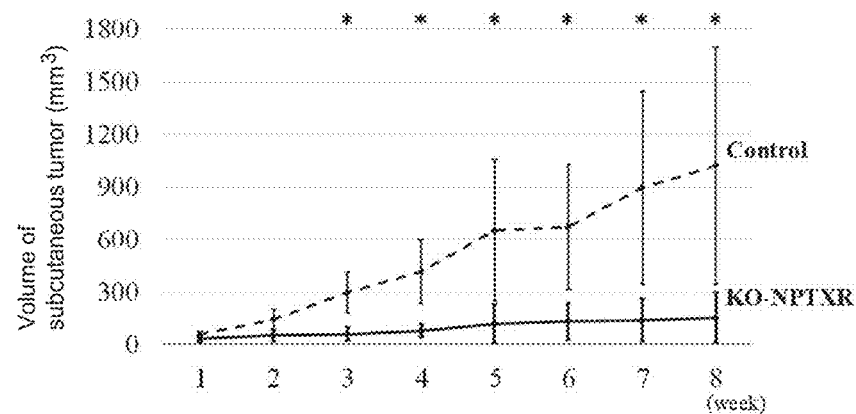

Mouse subcutaneous tumor models were made, and the tumorigenic abilities were compared, which revealed that, while a tumor increased over time in the control (untreated MKN1), a significant difference in the tumor volume (indicated by * in FIG. 8) was found in the CHRNB2 knockout cells on and after the fourth week from the inoculation, and the tumorigenic ability was reduced by knockout of CHRNB2 (FIG. 8(A)). Further, in the mice implanted with the NPTXR knockout cells, a significant difference in the tumor volume was found on and after the third week from the implantation, which revealed that the tumorigenic ability was decreased (FIG. 8(B)).

In mouse subcutaneous tumor models, the significant decrease in the growth of a tumor in the CHRNB2 or NPTXR knockout cells implies that medicines targeting these molecules have the inhibiting effect against the tumor. Accordingly, a neutralizing antibody and a nucleic acid medicine for these molecules were prepared, and the effects thereof were studied.

3. Preparation of CHRNB2 and NPTXR Molecular Target Drug (1) Preparation of Antibody Medicine Example 1

<Preparation of CHRNB2 Neutralizing Antibodies (Polyclonal Antibody)>

It was verified whether or not the activity of stomach cancer cells can be inhibited by activating a CHRNB2 specific antibody to inhibit the activity thereof. Estimation of the hydrophilicity, the secondary structure, and the antigenicity and optimal antigen site search were performed by using an epitope search tool (by Cosmo Bio). The following two sequences were selected as target sequences, rabbits were immunized in accordance with a routine method, and two types of polyclonal antibodies against CHRNB2 (Accession NO: NP_000739) were prepared. Note that the CHRNB2 antibody-1 and the CHRNB2 antibody-2 were antibodies obtained by immunizing amino acid sequences at positions 94-111 (Target sequence 1, SEQ ID NO: 8) and at positions 490-502 (Target sequence 2, SEQ ID NO: 9), respectively.
Target sequences;

```
                            (SEQ ID NO: 8)
CHRNB2 antibody-1:   WKPEEFDNMKKVRLPSKH (SEQ ID NO: 9)
CHRNB2 antibody-2:   TFLHSDHSAPSSK
```

Figure 9:
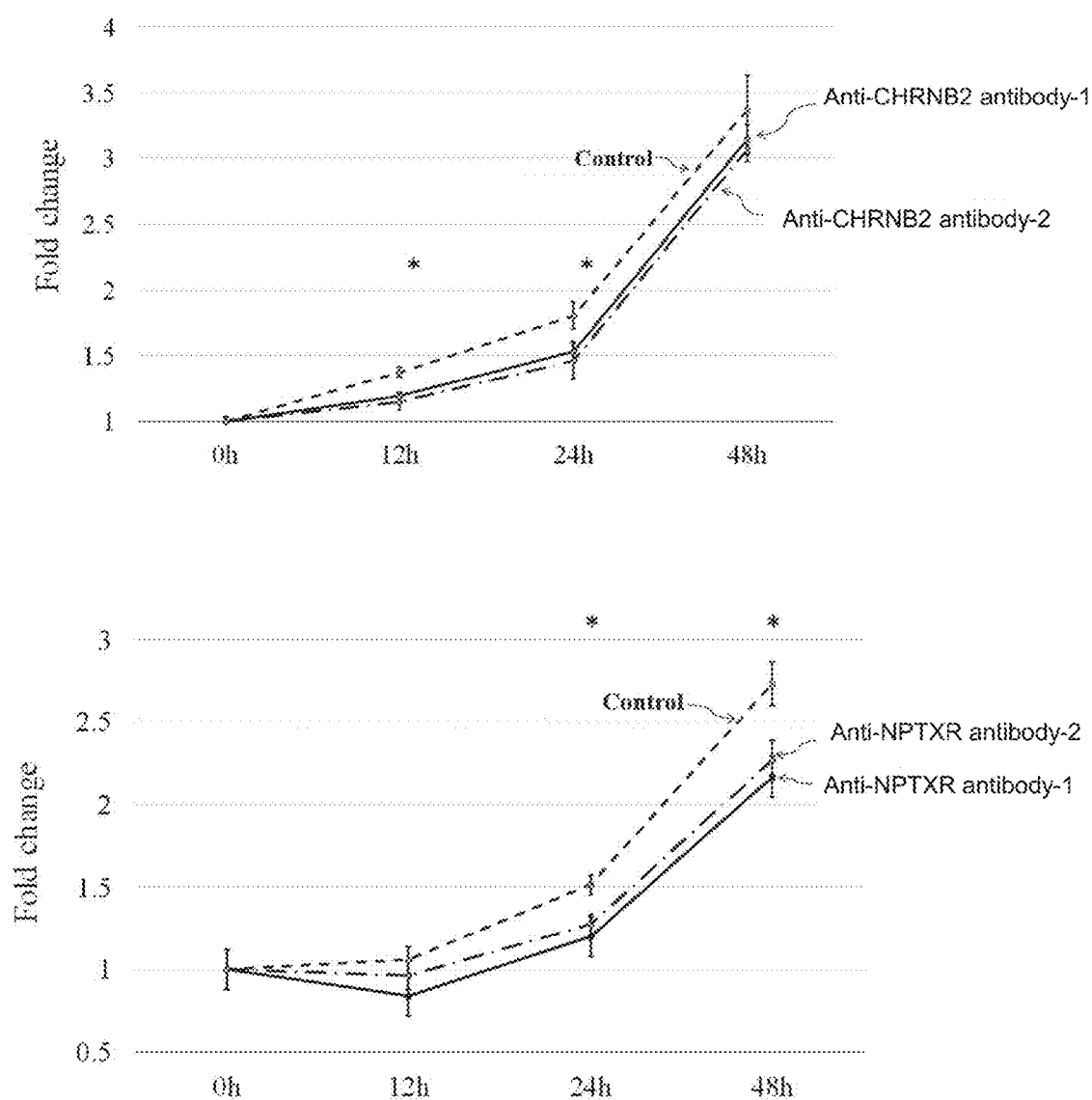
FIG. 9 is a diagram illustrating an analysis result of effects of an anti-CHRNB2 antibody and an anti-NPTXR antibody on cell proliferation.

First, it was examined whether or not the antibodies against these target sequences inhibit in vitro proliferation of stomach cancer cell line MKN1. MKN1 cells were seeded in a 96-well plate so that $1 \times 10^4$ cells were placed, each antibody was added to have a concentration of 0.7 μg/mL, and the cell proliferation was determined over time by WST-1 assay (FIG. 9, the upper). Note that a pre-bleed serum was used as a control. Two types of CHRNB2 antibodies were added to the stomach cancer cells, MKN1, and it was then observed that, in both the cases where the antibody against the target sequence 1 was used and the antibody against the target sequence 2 was used, the MKN1 cells exhibited significant (*) cell proliferation inhibition after 12 hours.

Example 2

<Preparation of NPTXR Neutralizing Antibody (Polyclonal Antibody)>

To verify whether or not the activity of stomach cancer cells can be inhibited by an NPTXR specific antibody to inhibit the activity thereof, estimation of the hydrophilicity, the secondary structure, and the antigenicity and optimal antigen site search were performed similarly by using an epitope search tool. The following two sequences were selected as target sequences, rabbits were immunized in accordance with a routine method, and two types of polyclonal antibodies against NPTXR (Accession NO: NP_055108) were prepared. Note that the NPTXR antibody-1 and the NPTXR antibody-2 were antibodies against amino acid sequences at positions 161-178 (Target sequence 1, SEQ ID NO: 10) and at positions 251-268 (Target sequence 2, SEQ ID NO: 11), respectively.
Target Sequences;

```
                            (SEQ ID NO: 10)
NPTXR antibody-1:    CESGLPRGLQGAGPRRDT (SEQ ID NO: 11)
NPTXR antibody-2:    KERVALSHSSRRQRQEVE
```

Analysis of in vitro cell proliferation inhibiting activity by antibodies against these target sequences was performed in the same manner (FIG. 9, the lower). Two types of NPTXR antibodies were added to the stomach cancer cells, MKN1, and it was then observed that, in both the cases where the antibody against the target sequence 1 was used and the antibody against the target sequence 2 was used, the MKN1 cells exhibited significant (*) cell proliferation inhibition after 24 hours.

Example 3

<Study of the Effect of CHRNB2 Neutralizing Antibodies by Using Mouse Peritoneal Dissemination Model>

Next, the effect of CHRNB2 antibodies that recognize the above two types of targets were analyzed by using mouse peritoneal dissemination models. The therapeutic effect was examined by intraperitoneally inoculating $1 \times 10^6$ MKN1 cells to 8-week old nude mice (BALB c nu/nu, obtained from Japan SLC). Note that four mice were used for each group, the CHRNB2 antibodies (CHRNB2 antibody-1: 6.5 μg/500 μL, CHRNB2 antibody-2: 8.7 μg/500 μL) were intraperitoneally administered twice a week for six weeks, respectively, as indicated by the administration schedule illustrated in FIG. 10, and the amount of stomach cancer peritoneal dissemination were compared with that of the control group. Note that the control is a group without antibody administration.

Figure 10:
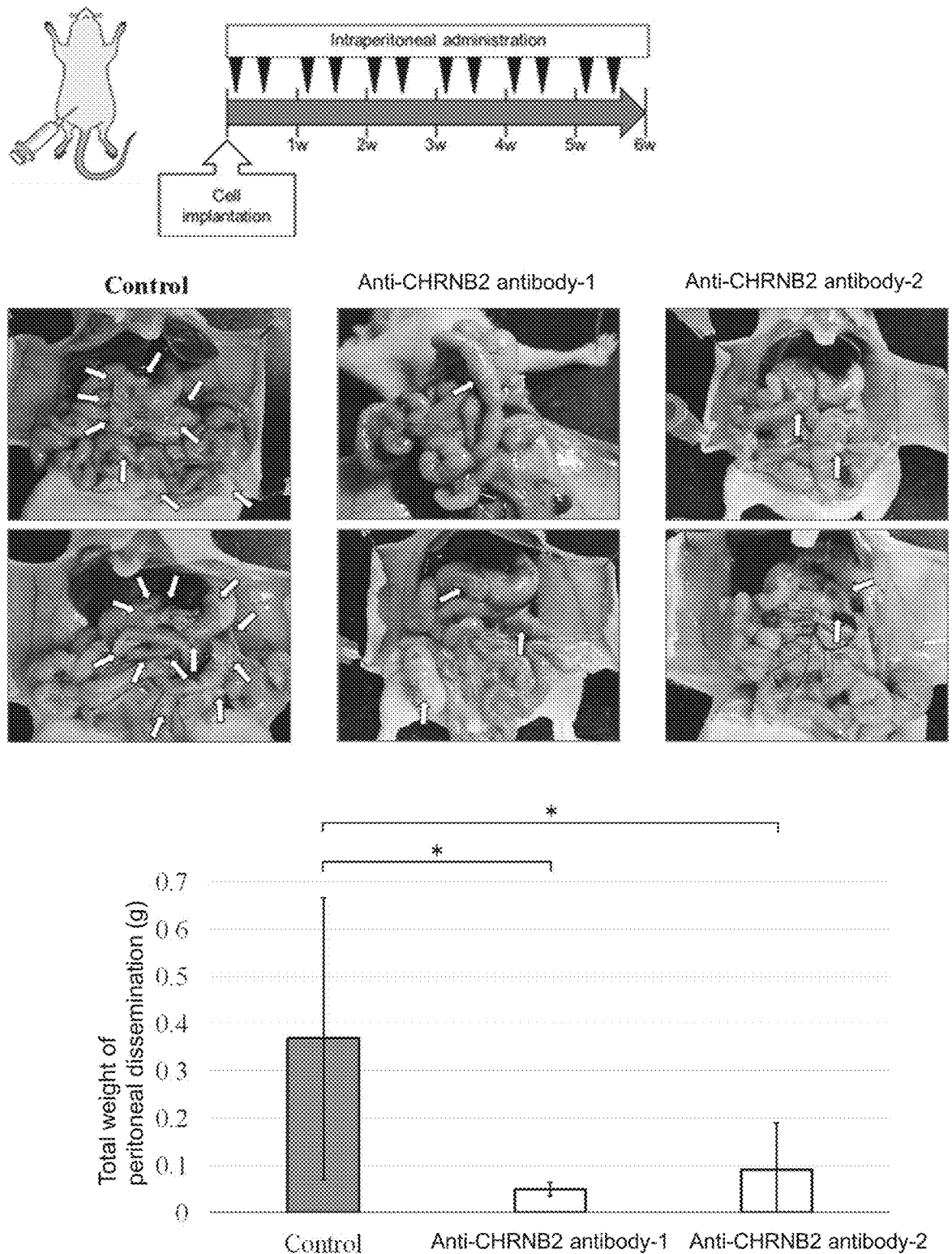
FIG. 10 is a diagram illustrating an analysis result of the effect of an anti-CHRNB2 antibody in a mouse peritoneal dissemination model.

For laparotomy macroscopic findings in six weeks of the control group, the CHRNB2 antibody-1-treated group, and the CHRNB2 antibody-2-treated group are indicated (FIG. 10, photographs). In the macroscopic findings, the positions where peritoneal dissemination was observed are indicated by arrows. In the CHRNB2 antibody-treated group, only few peritoneal dissemination nodules were observed when any of both the antibodies was used, and the therapeutic effect thereof was exhibited.

The dissemination nodules were retrieved from the mice subjected to laparotomy, and the total weight of the dissemination nodule in each mouse was determined (FIG. 10, the lower). In the antibody-treated groups, the total tumor weight was reduced significantly (*) compared to the control.

Example 4

<Examination of the Effect of NPTXR Neutralizing Antibodies by Using Mouse Peritoneal Dissemination Model>

Figure 11:
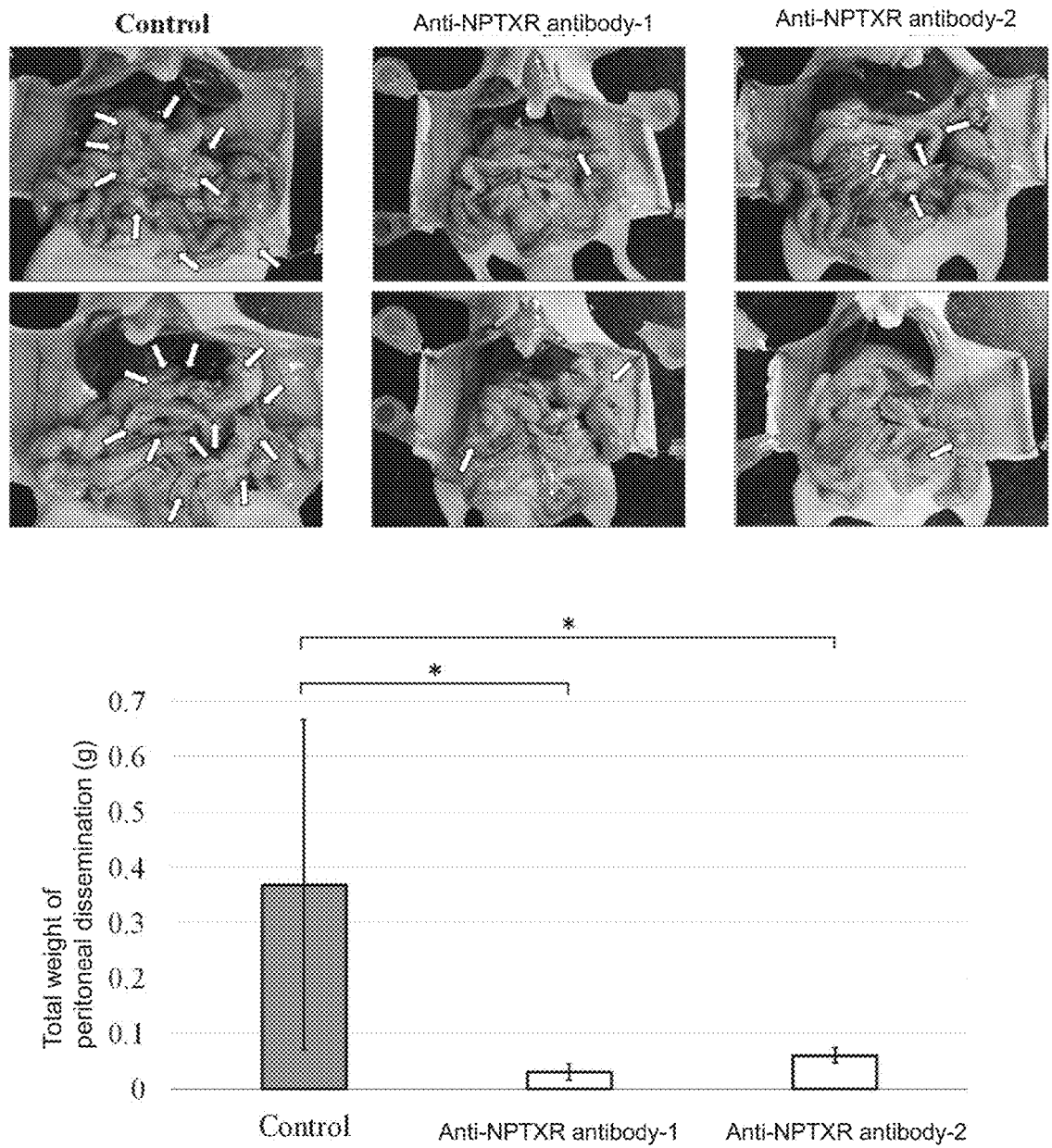
FIG. 11 is a diagram illustrating an analysis result of the effect of an anti-NPTXR antibody in a mouse peritoneal dissemination model.

In the same manner as in Example 3, the effect of NPTXR antibodies that recognize the targets of two regions of NPTXR were analyzed by using mouse peritoneal dissemination models (FIG. 11).

Laparotomy macroscopic findings obtained after six-week treatment of the control group, the NPTXR antibody-1-treated group, and the NPTXR antibody-2-treated group are indicated (FIG. 11, the upper). In the NPTXR antibody-treated group, only few peritoneal dissemination nodules were observed when any of both the antibodies was used, and the therapeutic effect thereof was exhibited.

Further, the dissemination nodules were retrieved from the mice subjected to laparotomy, and the total weight of the dissemination nodule in each mouse was determined (FIG. 11, the lower). In the antibody-treated groups, the total tumor weight was reduced significantly (*) compared to the control.

As indicated both the in vitro systems shown in Examples 1 and 2 and the in vivo systems shown in Examples 3 and 4, it is possible to significantly inhibit proliferation of cancer cells by targeting CHRNB2 or NPTXR and neutralizing the expression thereof. Therefore, a use of an antibody that recognizes CHRNB2 or NPTXR as a medicine enables treatment of recurrent or metastatic stomach cancer.

Furthermore, as described above, expression of CHRNB2 or NPTXR increases not only in the stomach cancer but also in many other cancers. There is a high likelihood that these cancers can be treated by using the neutralizing antibody of CHRNB2 or NPTXR in the same manner.

Example 5

<Establishment of Anti-CHRNB2 Monoclonal Antibody>

Figure 12:
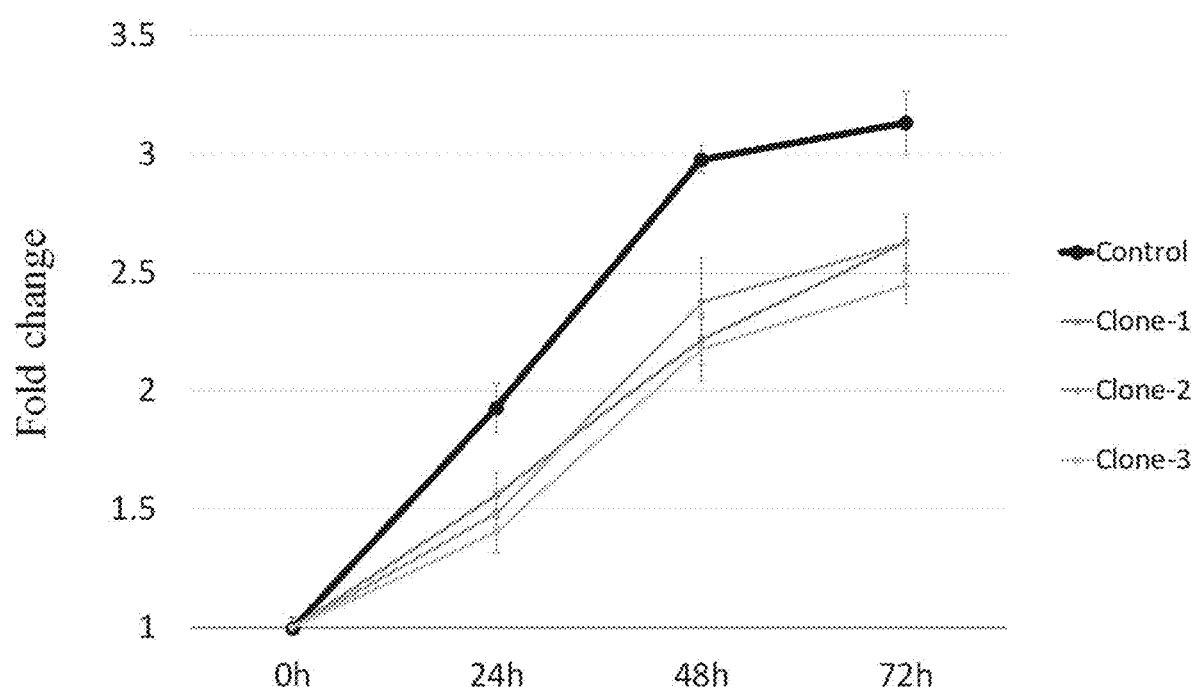
FIG. 12 is a diagram illustrating an analysis result of the effect of an anti-CHRNB2 monoclonal antibody on cell proliferation.

The peptide represented by SEQ ID NO: 9 was used as an antigen, and a monoclonal antibody against CHRNB2 was established by a routine method. Three clones were selected from the obtained hybridoma, and monoclonal antibodies were obtained. In the same manner as in Example 1, MKN1 cells were seeded in a 96-well plate so that 1×10⁴ cells were placed thereon, each antibody was added to have a concentration of 0.7 μg/mL, and the cell proliferation was determined over time by WST-1 assay (FIG. 12). All the antibodies obtained from any of the clones exhibited the same inhibiting effect against cell proliferation.

Among the above, the clone 3 (hereafter, referred to as CH-01) has been deposited to National Institute of Technology and Evaluation (NITE), NITE Patent Microorganisms Depositary (NPMD) (Room 122, 2-5-8 Kazusa-Kamatari, Kisarazu City, Chiba, Japan) on Jan. 23, 2019 (depository date) as Accession No. NITE P-02857.

<Effect of CH-01 Antibody on Mouse Peritoneal Dissemination Model>

Figure 13:
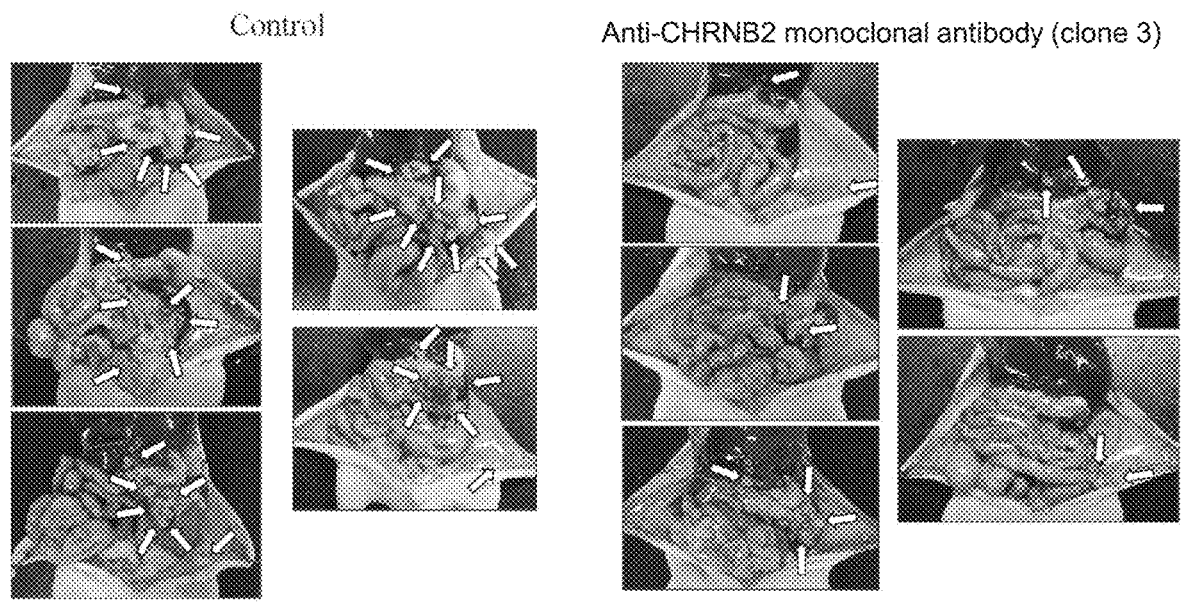
FIG. 13 is a diagram illustrating an analysis result of the peritoneal dissemination therapeutic effect of intraperitoneal administration of an anti-CHRNB2 monoclonal antibody.
Figure 13:
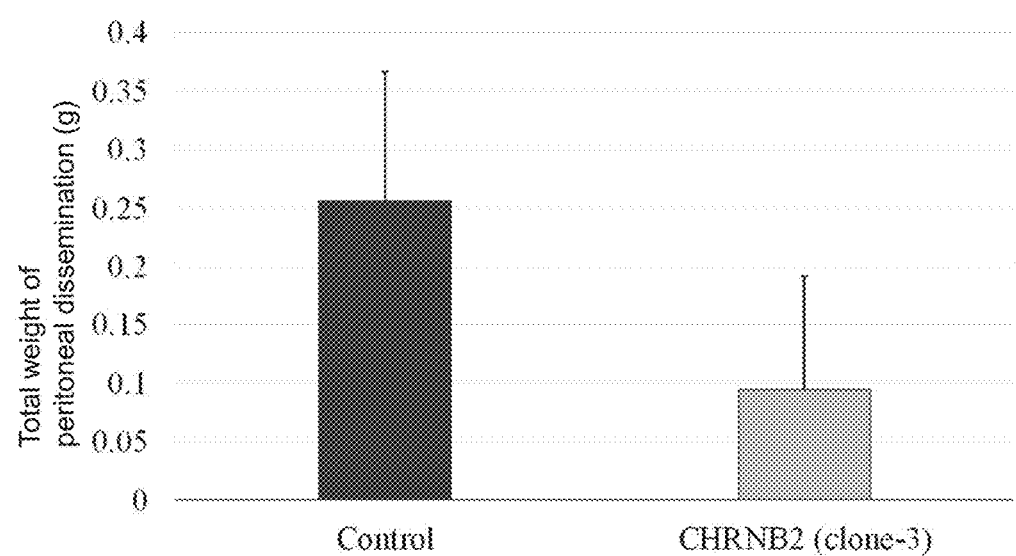

The therapeutic effect of the anti-CHRNB2 monoclonal antibody (clone 3, CH-01) on a mouse peritoneal dissemination model was examined (FIG. 13). The therapeutic effect was examined by intraperitoneally inoculating 2×10⁶ MKN1 cells to 8-week old nude mice (BALB c nu/nu). Twenty five μg/500 μl of the anti-CHRNB2 monoclonal antibody was intraperitoneally administered three times a week for four weeks, and the amount of stomach cancer peritoneal dissemination was compared with that of the non-treated group (n=5 in each group).

In the anti-CHRNB2 monoclonal antibody-treated group, clear inhibition of peritoneal dissemination progress was observed macroscopically (FIG. 13, the upper). Furthermore, stomach cancer peritoneal dissemination nodules were retrieved to compare the weight, and the total tumor weight was notably reduced in the anti-CHRNB2 monoclonal antibody-treated group (FIG. 13, the lower).

Example 6

<Establishment of Anti-NPTXR Monoclonal Antibody>

Figure 14A:
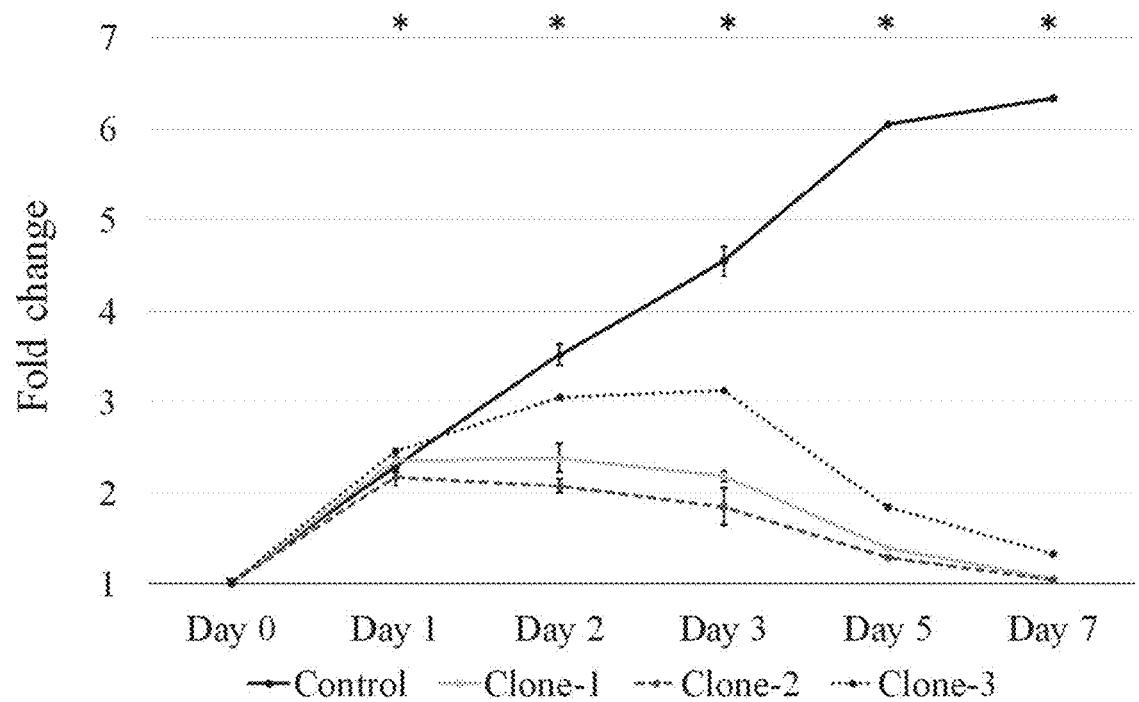
FIG. 14 is a diagram of study of the effect of an anti-NPTXR monoclonal antibody on cell proliferation. (A) is a diagram illustrating an analysis result obtained by using MKN1 cells. (B) is a diagram illustrating an analysis result obtained by using a cancer cell line derived from various organs other than MKN1 cells.

The peptide represented by SEQ ID NO: 10 was used as an antigen, and a monoclonal antibody against NPTXR was established by a routine method. In the same manner as in Example 1, MKN1 cells were seeded in a 96-well plate so that 1×10⁴ cells were placed thereon, each antibody was added to have a concentration of 0.7 μg/mL, and the cell proliferation was determined over time by WST-1 assay (FIG. 14(A)). All the clones exhibited the same inhibiting effect against cell proliferation.

Figure 14B:
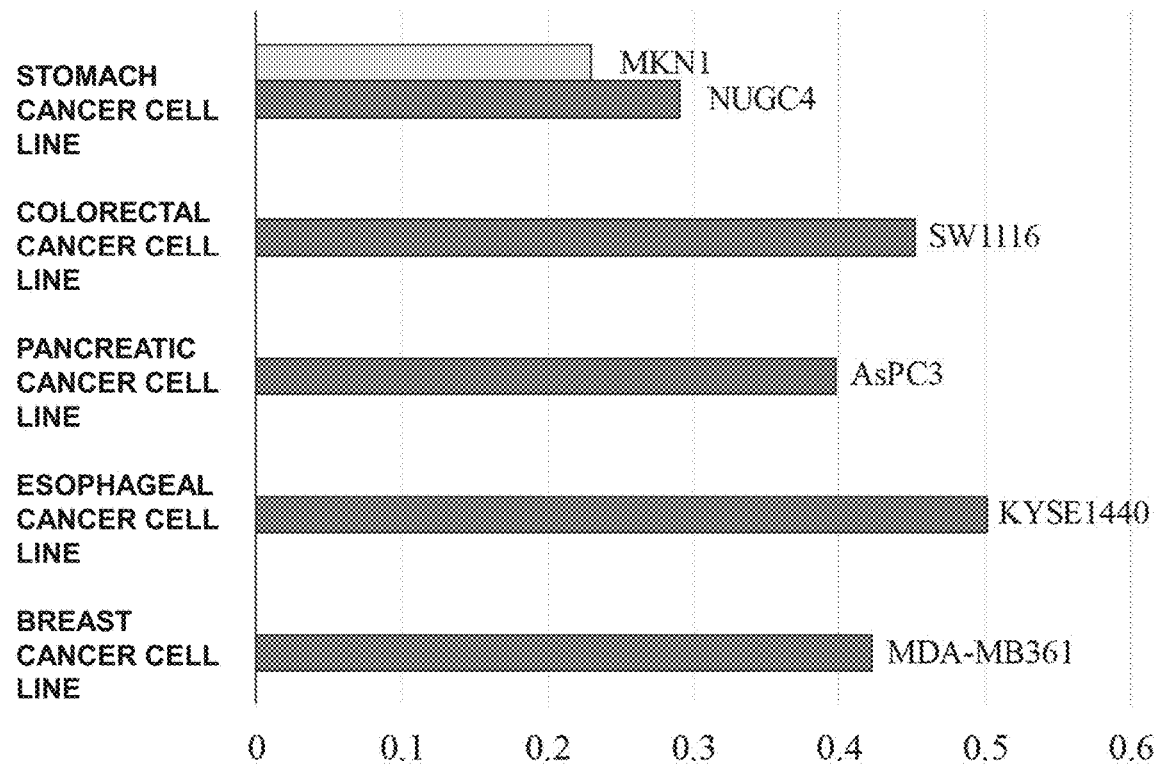

Furthermore, the effect of anti-NPTXR monoclonal antibody clone 1 was analyzed on cancer cell lines derived from various organs. To respective cancer cell lines, the antibody was added in the same manner as described above, and the proliferative ratio of the fifth day antibody-treated group relative to the control was calculated (FIG. 14(B)). It was indicated that proliferation of cells was inhibited by the antibody addition in all the cell lines. In particular, a strong inhibitory effect on cell proliferation of the antibody was found for MKN1 and NUGC4 that are cell lines established from stomach cancer.

<Effect of Anti-NPTXR Monoclonal Antibody on Mouse Peritoneal Dissemination Model>

Figure 15:
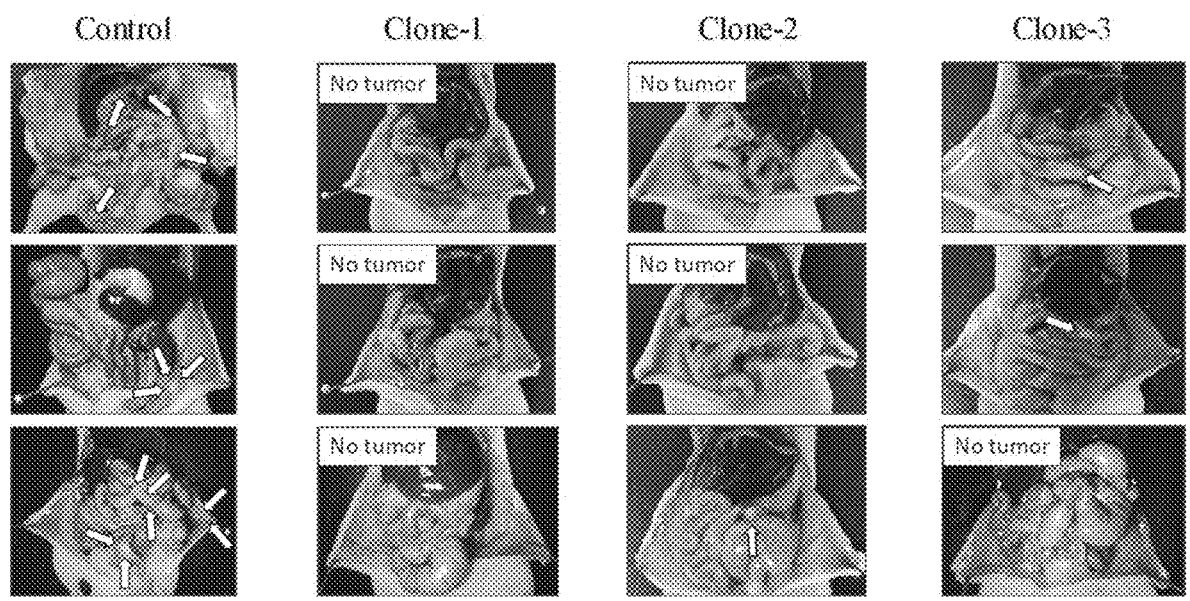
FIG. 15 is a diagram illustrating an analysis result of therapeutic effect on the peritoneal dissemination of intraperitoneal administration of an anti-NPTXR monoclonal antibody.
Figure 15:
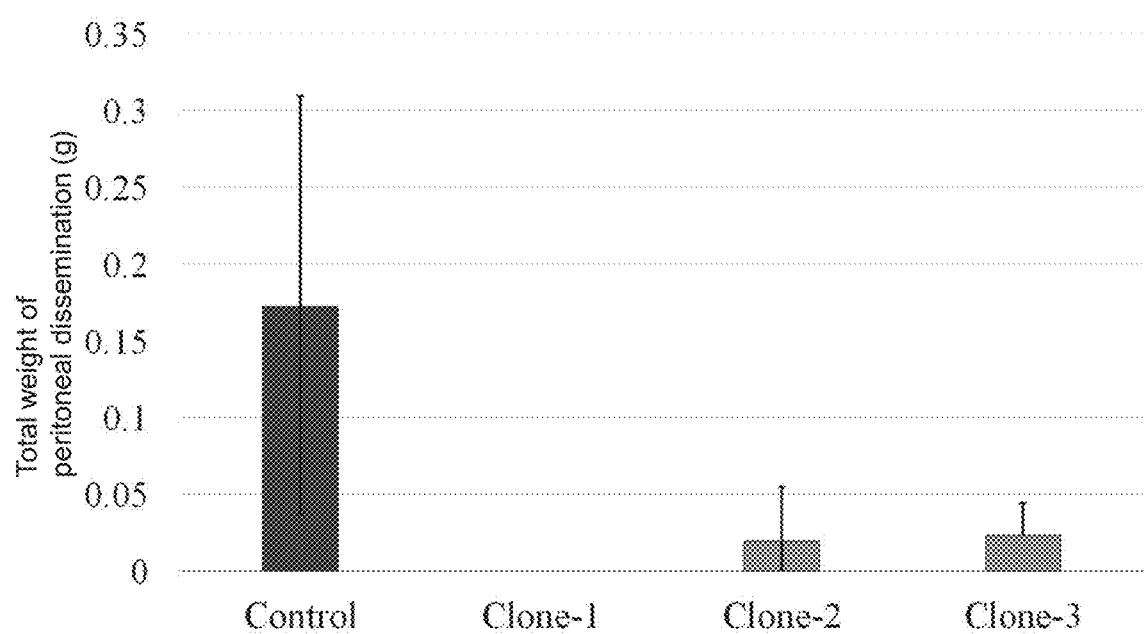

The therapeutic effect of the anti-NPTXR monoclonal antibody on a mouse peritoneal dissemination model was examined (FIG. 15). The therapeutic effects of the antibodies obtained from the clones 1 to 3 were examined by intraperitoneally inoculating 2×10⁶ MKN1 cells to 8-week old nude mice (BALB c nu/nu). Twenty five μg/500 μl of the anti-NPTXR monoclonal antibody was intraperitoneally administered three times a week for two weeks, and the amount of stomach cancer peritoneal dissemination was compared with that of the non-treated group (n=3 in each group).

In the anti-NPTXR monoclonal antibody-treated group, clear inhibition of peritoneal dissemination progress was observed macroscopically (FIG. 15, the upper). In particular, no peritoneal dissemination lesion was macroscopically detected in the group of administration of the antibody obtained from the clone 1. Furthermore, stomach cancer peritoneal dissemination nodules were retrieved to compare the weight (FIG. 15, the lower). The total tumor weight was notably reduced in all the antibody-treated groups.

Note that the clone 1 (hereafter, referred to as NP-01) has been deposited to National Institute of Technology and Evaluation (NITE), NITE Patent Microorganisms Depositary (NPMD) (Room 122, 2-5-8 Kazusa-Kamatari, Kisarazu City, Chiba, Japan) on Mar. 12, 2019 (depository date under the Budapest Treaty) as Accession No. NITE P-02856.

<Epitope Mapping of NP-01 Antibody>

Epitope analysis of the NP-01 antibody was performed. In a region from positions 151 to 190 of NPTXR protein, the peptide consisting of 15 amino acids was synthesized while being shifted from the N-terminal to the C-terminal one by one, as shown in Table 2. Linkage to each peptide was determined by enzyme-linked immunosorbent assay, and epitopes were identified (Table 3). As a result, it was revealed that the amino acid sequence from positions 164 to 178, GLPRGLQGAGPRRDT (SEQ ID NO: 12) was intensively recognized as an epitope. Since it is considered that an antibody that recognizes the same epitope has a similar character, it is assumed that the antibody that recognizes the peptide represented by SEQ ID NO: 12 binds to NPTXR and has the effect of inhibiting proliferation of cancer cells.

TABLE 2

| Antigen No | 1888-1 | 1888-2 | 1888-3 | 1888-4 |
|---|---|---|---|---|
| Seq. Name | NPTXR (POS: 151-165) | NPTXR (POS: 152-166) | NPTXR (POS: 153-167) | NPTXR (POS: 154-168) |
| Antigen No | 1888-5 | 1888-6 | 1888-7 | 1888-8 |
| Seq. Name | NPTXR (POS: 155-169) | NPTXR (POS: 156-170) | NPTXR (POS: 157-171) | NPTXR (POS: 158-172) |
| Antigen No | 1888-9 | 1888-10 | 1888-11 | 1888-12 |
| Seq. Name | NPTXR (POS: 159-173) | NPTXR (POS: 160-174) | NPTXR (POS: 161-175) | NPTXR (POS: 162-176) |

TABLE 2-continued

| Antigen No | 1888-13 | 1888-14 | 1888-15 | 1888-16 |
|---|---|---|---|---|
| Seq. Name | NPTXR (POS: 163-177) | NPTXR (POS: 164-178) | NPTXR (POS: 165-179) | NPTXR (POS: 166-180) |
| Antigen No | 1888-17 | 1888-18 | 1888-19 | 1888-20 |
| Seq. Name | NPTXR (POS: 167-181) | NPTXR (POS: 168-182) | NPTXR (POS: 169-183) | NPTXR (POS: 170-184) |
| Antigen No | 1888-21 | 1888-22 | 1888-23 | 1888-24 |
| Seq. Name | NPTXR (POS: 171-185) | NPTXR (POS: 172-186) | NPTXR (POS: 173-187) | NPTXR (POS: 174-188) |
| Antigen No | 1888-25 | 1888-26 | Control | |
| Seq. Name | NPTXR (POS: 175-189) | NPTXR (POS: 176-190) | Antigen peptide | |

TABLE 3

| | 1 | 2 | 3 | 4 | 5 | 6 | 7 | 8 |
|---|---|---|---|---|---|---|---|---|
| Antigen No. | 1888-1 | 1888-2 | 1888-3 | 1888-4 | 1888-5 | 1888-6 | 1888-7 | 1888-8 |
| 1 | 0.044 | 0.060 | 0.054 | 0.055 | 0.071 | 0.070 | 0.065 | 0.071 |
| 2 | 0.047 | 0.054 | 0.055 | 0.054 | 0.065 | 0.066 | 0.072 | 0.068 |
| Average | 0.046 | 0.057 | 0.055 | 0.055 | 0.068 | 0.068 | 0.069 | 0.070 |
| Antigen No. | 1888-9 | 1888-10 | 1888-11 | 1888-12 | 1888-13 | 1888-14 | 1888-15 | 1888-16 |
| 1 | 0.142 | 0.060 | 1.318 | 1.410 | 1.459 | 1.501 | 1.193 | 0.545 |
| 2 | 0.154 | 0.069 | 1.353 | 1.499 | 1.413 | 1.457 | 1.113 | 0.515 |
| Average | 0.148 | 0.065 | 1.336 | 1.455 | 1.436 | 1.479 | 1.153 | 0.530 |
| Antigen No. | 1888-17 | 1888-18 | 1888-19 | 1888-20 | 1888-21 | 1888-22 | 1888-23 | 1888-24 |
| 1 | 0.490 | 0.097 | 0.104 | 0.184 | 0.072 | 0.062 | 0.062 | 0.058 |
| 2 | 0.397 | 0.085 | 0.090 | 0.179 | 0.073 | 0.039 | 0.076 | 0.057 |
| Average | 0.444 | 0.091 | 0.097 | 0.182 | 0.073 | 0.066 | 0.069 | 0.058 |
| Antigen No. | 1888-25 | 1888-26 | Control | | | | | |
| 1 | 0.047 | 0.055 | 1.457 | | | | | |
| 2 | 0.061 | 0.064 | 1.506 | | | | | |
| Average | 0.054 | 0.060 | 1.482 | | | | | |

(2) Preparation of Nucleic Acid Medicine

Example 7

<Study of Nucleic Acid Medicine Against CHRNB2>

It was analyzed whether or not proliferation of stomach cancer cells can be inhibited by using a nucleic acid medicine to inhibit CHRNB2 expression. The siRNA specific to CHRNB2 was used to analyze in vitro the effect on the proliferative ability. Both the siRNA of CHRNB2 (si-CHRNB2) and the control siRNA (siControl) were obtained from Hokkaido System Science. Further, the control represents proliferation of untreated cells.

Figure 16A:
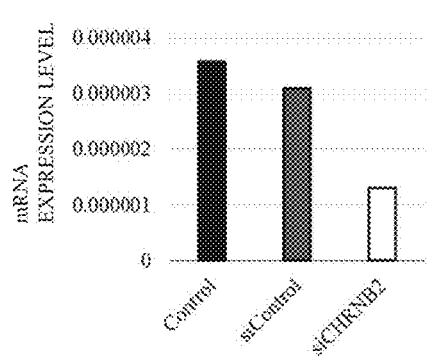
FIG. 16 shows diagrams indicating analysis results of the effect of (A) CHRNB2 and (B) NPTXR on cell proliferation of a siRNA.
Figure 16A:
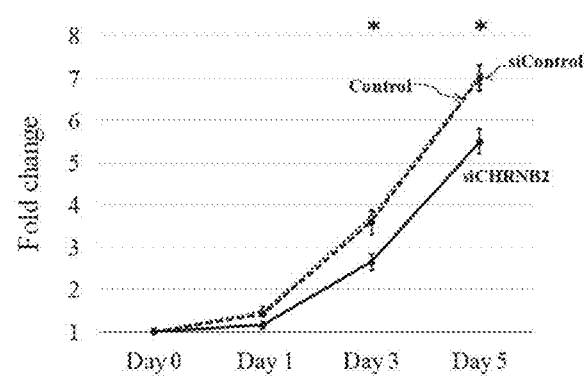

The siRNA was introduced to MKN1 cells by using LipoTrust (registered trademark) EX Oligo (by Hokkaido System Science), then cultured in a serum-free DMEM medium for 72 hours, and the proliferative ability thereof was evaluated (FIG. 16(A)).

The left graph shows a result of analysis of the CHRNB2 mRNA expression level by quantitative PCR, and the right graph shows a result of the cell proliferation analyzed by Cell Counting Kit-8. The proliferative ability of stomach cancer cells was reduced significantly (*) by the siRNA specific to CHRNB2.

Example 8

<Study of Nucleic Acid Medicine Against NPTXR>

Figure 16B:
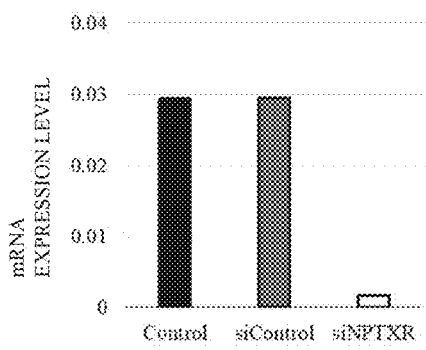
Figure 16B:
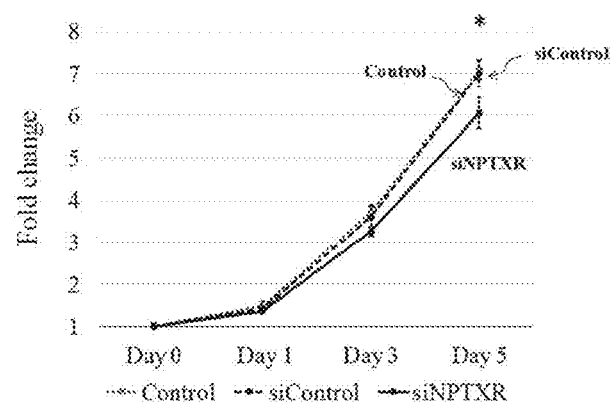

Next, the siRNA specific to NPTXR was used to analyze in vitro the effect on the proliferative ability in the same manner as in Example 7. The siRNA of NPTXR was introduced to MKN1 cells, then cultured in a serum-free DMEM medium for 72 hours, and the proliferative ability was then evaluated (FIG. 16(B)).

The left graph shows a result of analysis of the NPTXR mRNA expression level by quantitative PCR, and the right graph shows a result of the cell proliferation analyzed by Cell Counting Kit-8. The proliferative ability of stomach cancer cells was reduced significantly (*) by the siRNA specific to NPTXR.

The above results revealed that inhibition of mRNA expression enables inhibition of cell proliferation for both cases of CHRNB2 and NPTXR. As with antibody medicines, it is possible to inhibit the progression of cancers by using the nucleic acid medicine to inhibit expression of these molecules.

4. CHRNB2, NPTXR Expression Analysis Using Human Clinical Data

In the case of clinical use of a medicine targeting CHRNB2 or NPTXR, unnecessary treatment may be avoided by confirming the expression of CHRNB2 or NPTXR in advance and treating only the patients having enhanced expression in their tumor tissues. The mRNA expression level of CHRNB2 or NPTXR in stomach cancer tissues was analyzed by resected specimens. Further, the correlation between prognosis and the mRNA expression level was evaluated by ROC curve analysis, and it was examined whether or not the mRNA expression level can be used in prognosis forecast.

Example 9

<Quantitative Analysis of CHRNB2 Expression Level in Stomach Cancer Tissue>

Figure 17A:
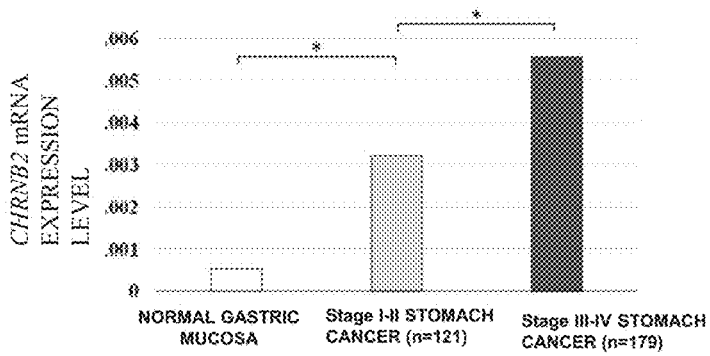
FIG. 17 is a diagram of analysis of expression of CHRNB2 in stomach cancer patients. (A) is a diagram illustrating an mRNA expression level based on a stage, (B) is a diagram illustrating ROC curve analysis of an mRNA expression level for recurrence and death, (C) is a diagram illustrating a relationship between a calculated cut-off value and prognosis, and (D) is a diagram illustrating an analysis result of protein expression in a stomach cancer tissue.

To confirm reproducibility of the exhaustive analysis data, the mRNA expression level of CHRNB2 in stomach cancer tissues obtained from 300 stomach cancer cases was examined by a quantitative PCR method. The CHRNB2 expression in the tissues obtained from normal gastric mucosa, 121 cases of stomach cancer of stages I and II, and 179 cases of stomach cancer of stages III and IV was determined by quantitative PCR (FIG. 17(A)).

The expression of CHRNB2 was higher in the stomach cancer tissues than in the normal gastric mucosa and increased more significantly in stages III and IV than in stages I and II. From these data, it is understood that the expression of CHRNB2 is increased as the stage progresses.

Figure 17B:
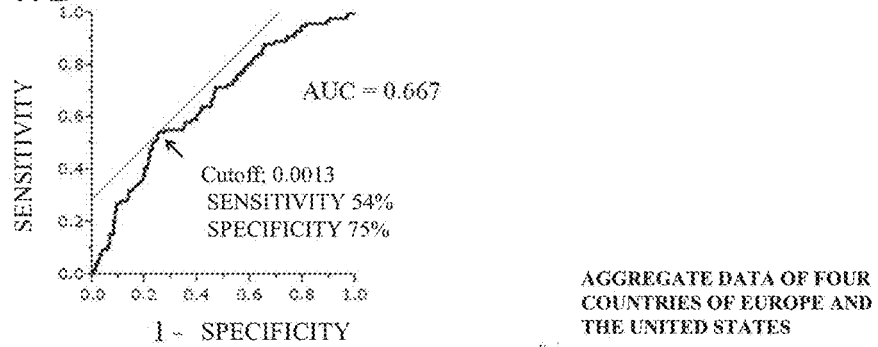
Figure 17C:
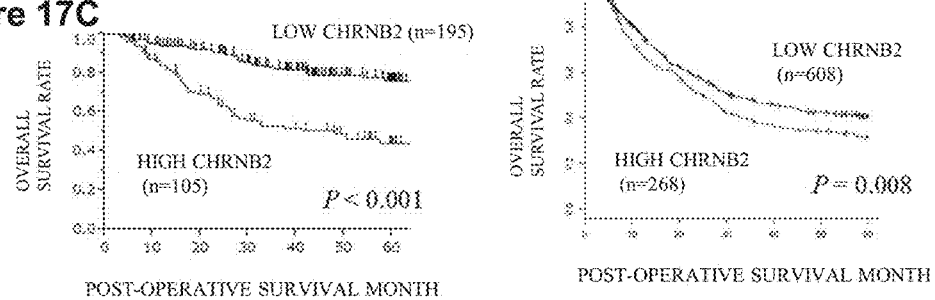

The cut-off value of the CHRNB2 mRNA expression level in the stomach cancer primary lesion tissue with respect to recurrence and death was found by ROC curve analysis. A result of the sensitivity of 54%, the specificity of 75%, and AUC=0.667 was obtained when the cut-off value was set at 0.0013 (FIG. 17(B)). This result was used to classify the 300 stomach cancer cases into a high CHRNB2 expression group and a low CHRNB2 expression group for analysis, and prognosis was significantly poor in the high CHRNB2 expression group (FIG. 17(C), left). This result was reproduced in aggregate data of four countries of Europe and the United States disclosed in a Web site (http://kmplot.com/analysis/) (FIG. 17(C), right). Therefore, the CHRNB2 expression can be used for prognosis forecast.

Figure 17D:
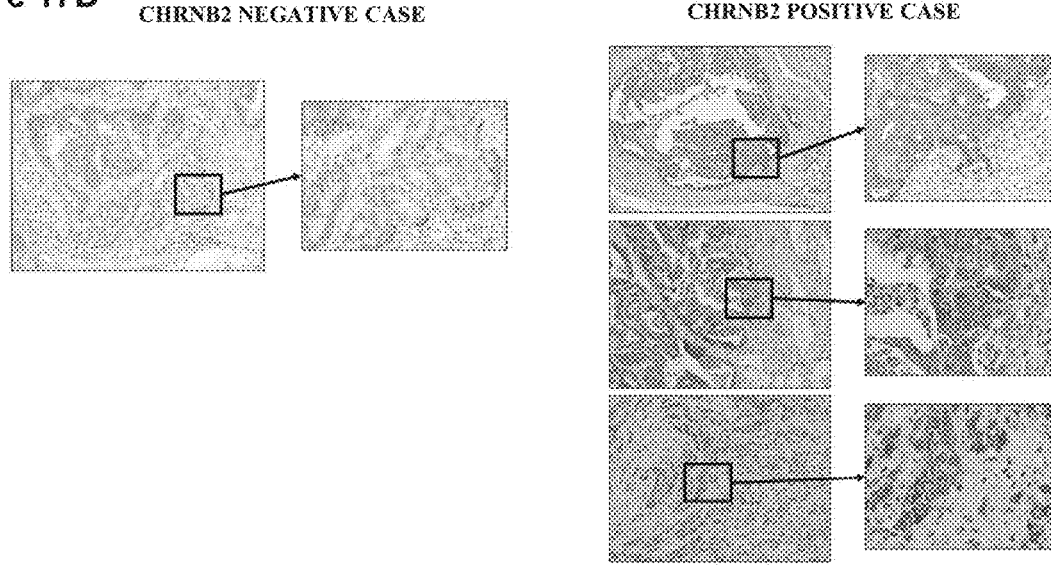

Furthermore, the CHRNB2 protein in gastric tissues was detected by an immunohistochemical staining (FIG. 17(D)). A polyclonal antibody against CHRNB2 was used to perform immunostaining of tissues by a routine method. It is possible to identify a case where the expression is clearly observed in tumor tissues and a case with no expression. Therefore, expression of a CHRNB2 protein can be observed by immunohistochemical staining.

Example 10

<Quantitative Analysis of NPTXR Expression Level in Stomach Cancer Tissue>

Figure 18A:
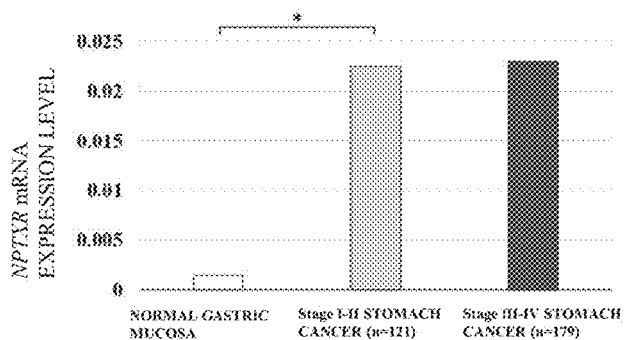
FIG. 18 is a diagram of analysis of expression of NPTXR in stomach cancer patients. (A) is a diagram illustrating an mRNA expression level based on a stage, (B) is a diagram illustrating ROC curve analysis of an mRNA expression level for recurrence and death, (C) is a diagram illustrating a relationship between a calculated cut-off value and prognosis, and (D) is a diagram illustrating an analysis result of protein expression in a stomach cancer tissue.

The mRNA expression level of NPTXR in stomach cancer tissues obtained from 300 stomach cancer cases was examined by a quantitative PCR method in the same manner as in Example 9 (FIG. 18(A)). The expression of NPTXR increased more significantly in the stomach cancer tissues than in the normal gastric mucosa regardless of the stage.

Figure 19:
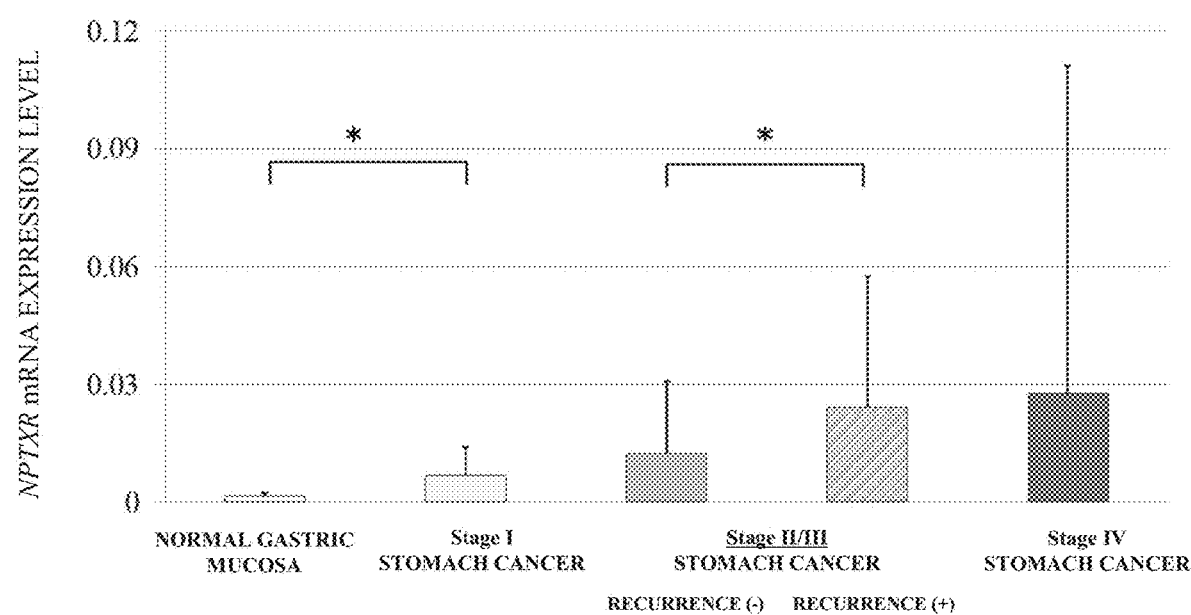
FIG. 19 is a diagram illustrating an analysis result of an NPTXR mRNA expression level in each stage in a stomach cancer patient tissue.

Furthermore, for NPTXR, the above 300 cases were classified in detail on a stage basis and were examined by the quantitative PCR method in the same manner as described above (FIG. 19). It was observed that the expression of NPTXR tends to be increased as the stage progresses, and it was observed that there is a significant difference between the expression in the normal tissues and stage I tissues and the expression in stages II and III tissues.

Figure 18B:
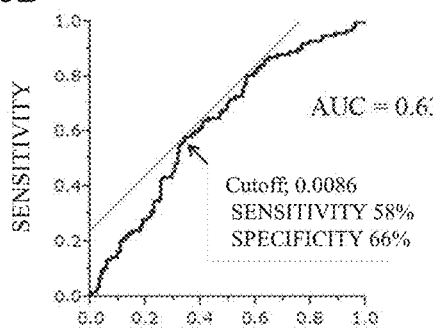
Figure 18C:
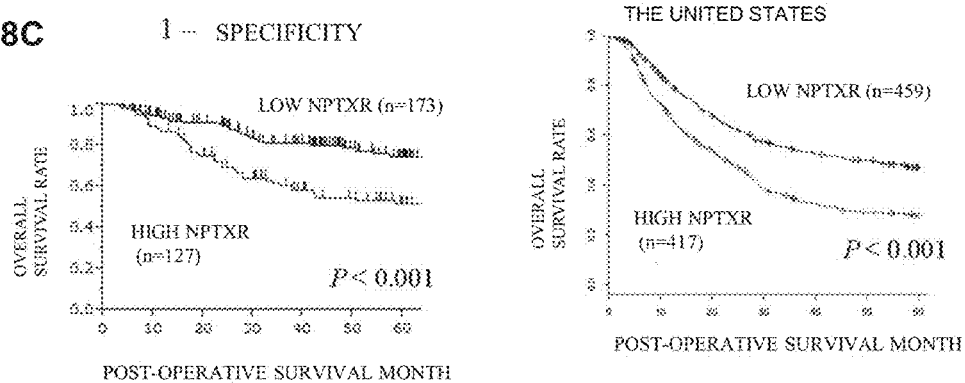
Figure 18C:
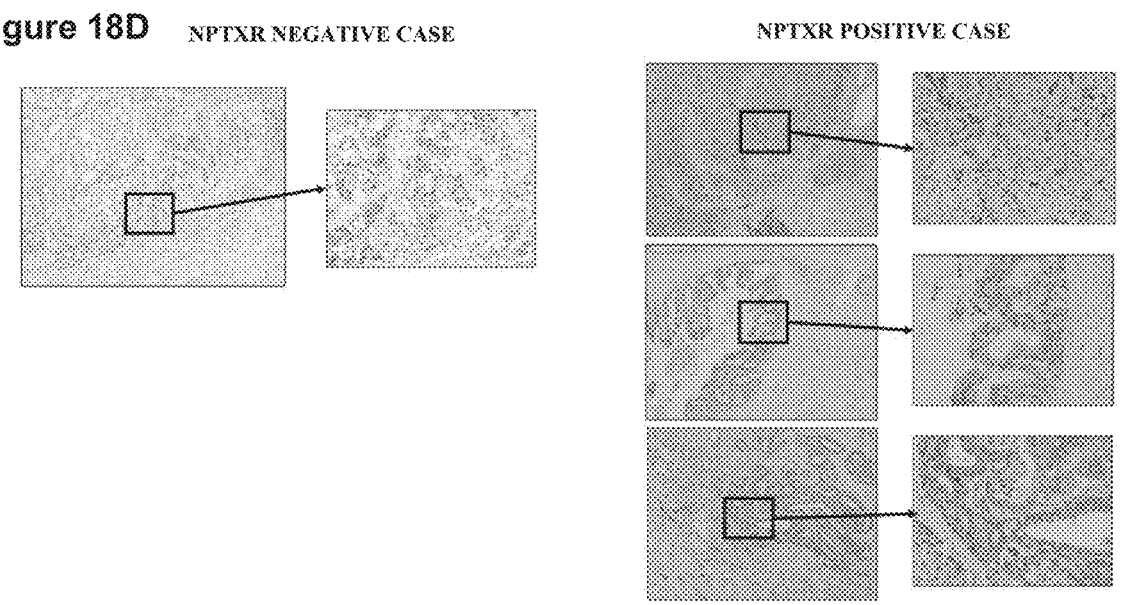

Furthermore, the cut-off value of the NPTXR mRNA expression level in the stomach cancer primary lesion tissue with respect to recurrence and death was found by ROC curve analysis. A result of the sensitivity of 58%, the specificity of 66%, and AUC=0.638 was obtained when the cut-off value is set at 0.0086 (FIG. 18(B)). This result was used to classify the 300 stomach cancer cases into a high NPTXR expression group and a low NPTXR expression group for analysis, and prognosis was significantly poor in the high NPTXR expression group (FIG. 18(C), left). This result was reproduced in aggregate data of four countries of Europe and the United States disclosed in a Web site (http://kmplot.com/analysis/) (FIG. 18(C), right). Therefore, the NPTXR expression can also be used for prognosis forecast.

Furthermore, the NPTXR protein in gastric tissues was detected by an immunohistochemical staining (FIG. 18(D)). A polyclonal antibody against NPTXR was used to perform immunostaining of tissues by a routine method. It is possible to identify a case where the expression is clearly observed in tumor tissues and a case with no expression. Therefore, expression of an NPTXR protein can be observed by immunohistochemical staining.

It was indicated that the CHRNB2 antibody or the NPTXR antibody can be applied to companion diagnosis that enables selection of applicable patients of molecular target treatment targeting CHRNB2 and NPTXR. Further, since CHRNB2 and NPTXR are proteins for which a difference in expression was observed in comparison with the long-term recurrence-free group and the recurrent metastasis group, CHRNB2 expression or NPTXR expression can also be used as a prognosis forecast marker. Immunohistochemical staining enables determination from a small amount of a tissue specimen and is thus applied not only to a surgery specimen but also to a biopsy specimen of endoscopic examination. Further, since immunohistochemical staining is a commonly performed clinical test, it is clinically significant to be able to confirm the expression of these proteins in a specimen by using an antibody.

Example 11

Figure 20A:
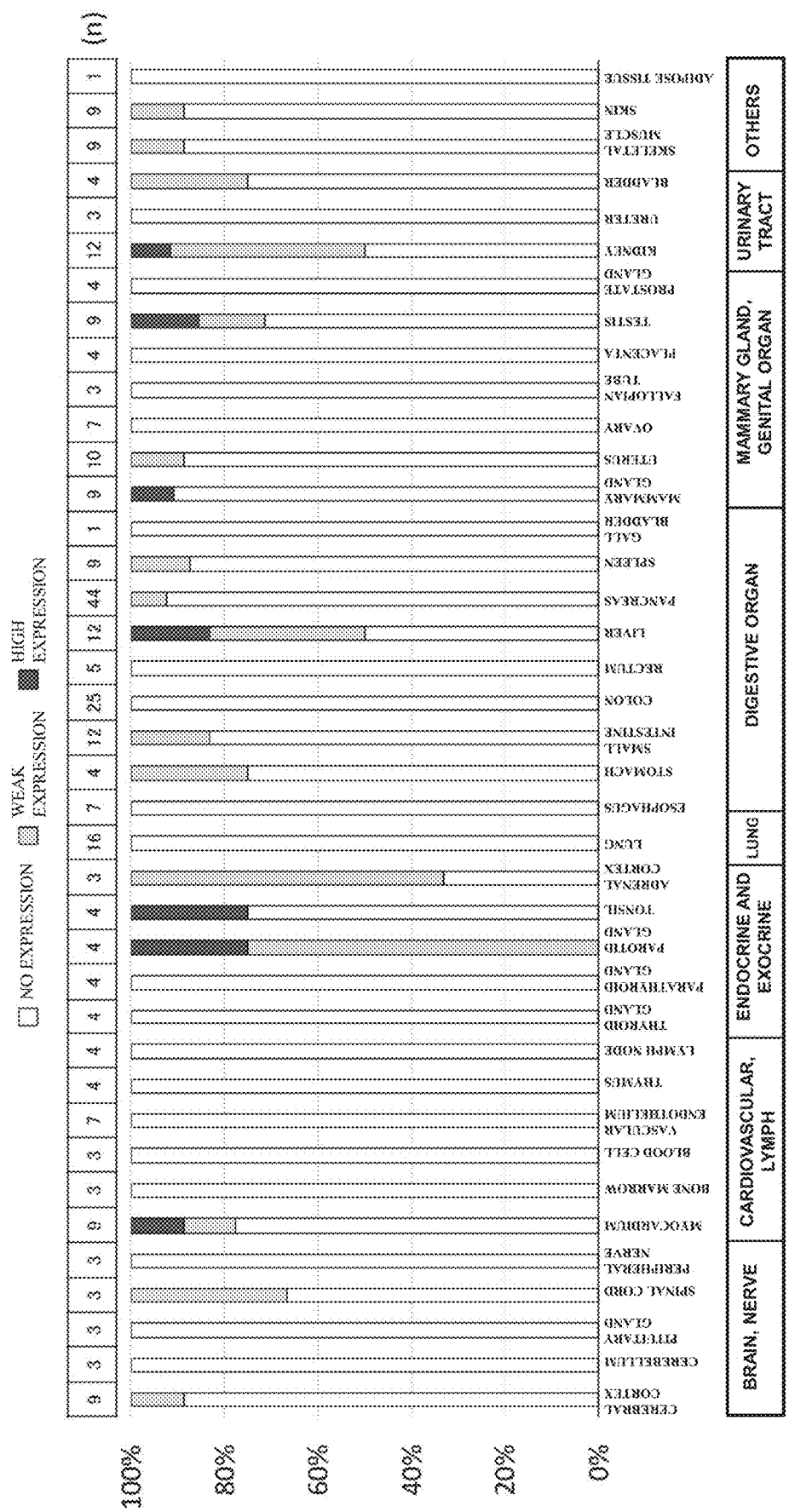
FIG. 20 shows results of analysis of an expression profile in normal tissues of various organs. (A) is a diagram illustrating CHRNB2 expression profile, and (B) is a diagram illustrating an NPTXR expression profile.
Figure 20B:
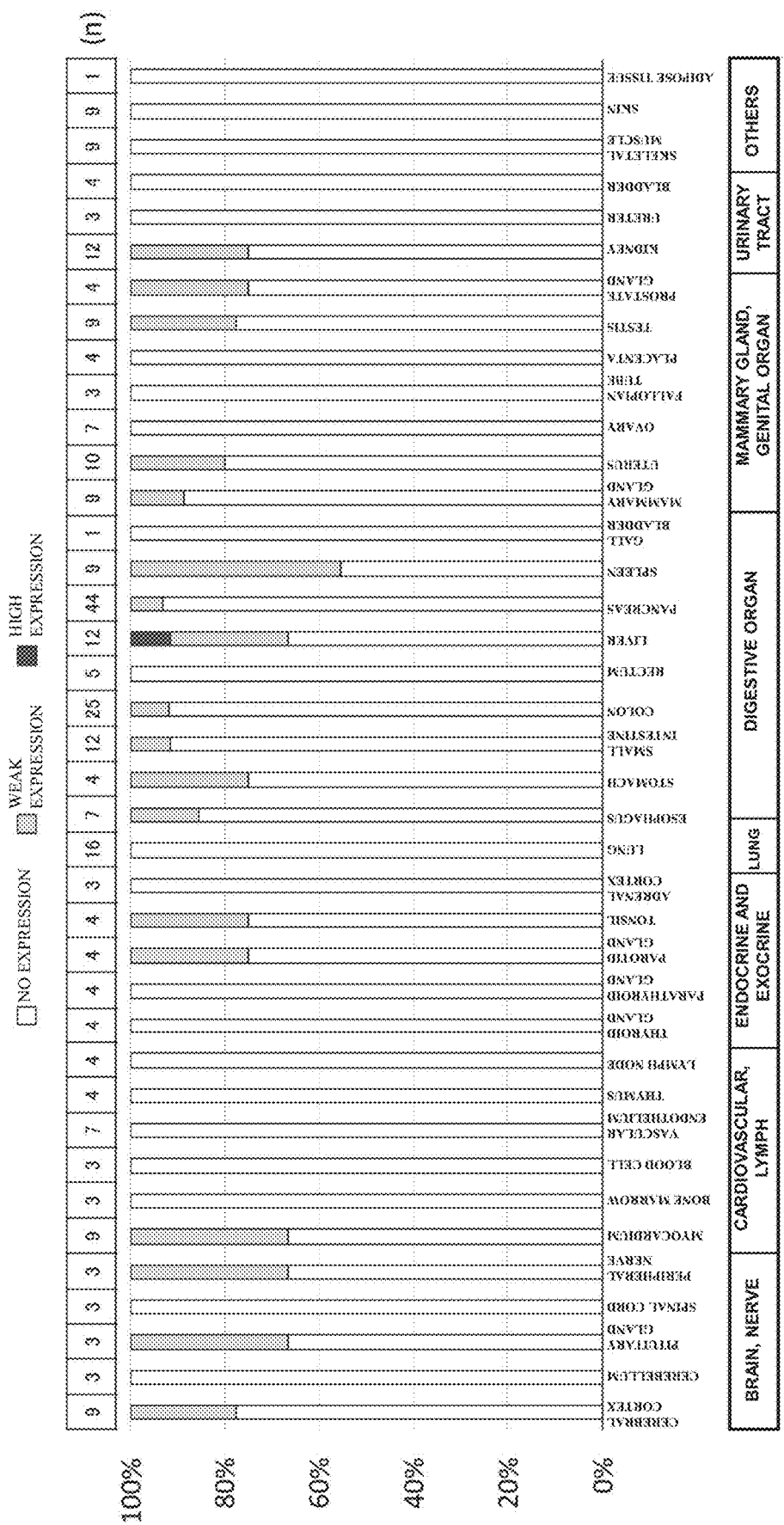

<Expression Profile by Tissue Microarray>
(1) Expression Profile in Various Organs and Normal Tissues As data used for considering safety in a case of using an antibody medicine binding to CHRNB2 or NPTXR or a medicine inhibiting the expression, the expression profiles in various organs and normal tissues of CHRNB2 and NPTXR were analyzed (FIG. 20).

The CHRNB2 expression and the NPTXR expression were analyzed by an immunohistochemical staining method by using a tissue microarray (by Provitro). As a result of tissue staining, the analyzed tissues are classified into no expression, low expression, and high expression, and the ratio thereof is indicated in the graph. Note that the number of analyzed tissues is represented as (n) on the graph. It is implied that both the CHRNB2 expression and the NPTXR expression are less in human normal tissues and it is suggested that the possibility of occurring an adverse event on an unintended organ is low.

2. Expression Profile in Cancers of Various Organs

Figure 21A:
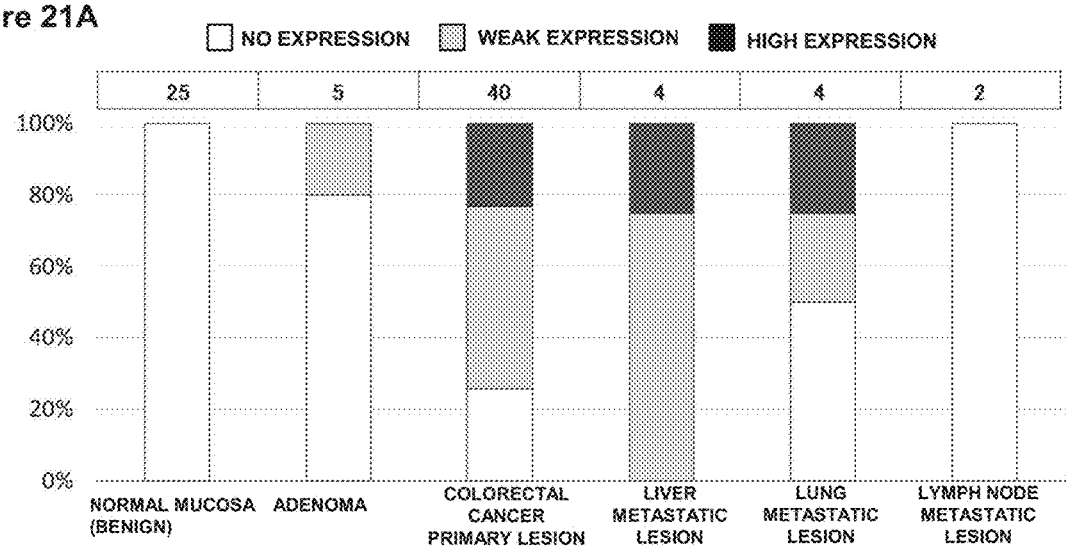
FIG. 21 is a diagram illustrating an expression analysis result in a colon. (A) shows a CHRNB2 expression profile, and (B) shows an NPTXR expression profile.
Figure 21B:
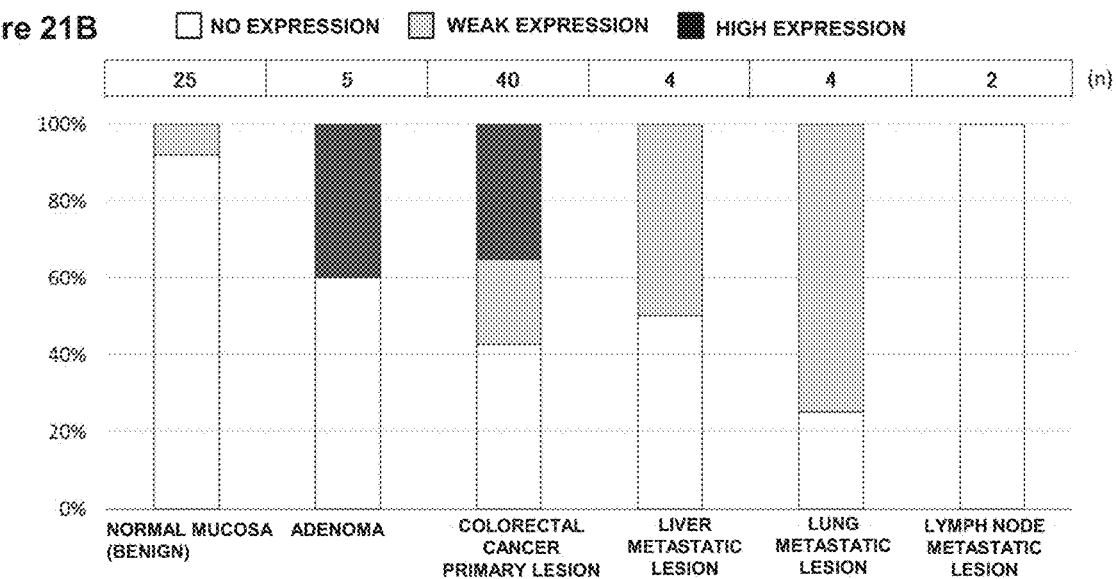

The CHRNB2 expression analysis and the NPTXR expression analysis in various cancers were performed by using a tissue microarray (by Provitro). In the same manner as described above, as a result of tissue staining, the analyzed tissues are classified into no expression, low expression, and high expression and indicated in the graph. The CHRNB2 expression analysis and the NPTXR expression analysis in colons were performed. The CHRNB2 expression was observed in approximately 70% of colorectal cancer, and the NPTXR expression was observed in approximately 50% of colorectal cancer (FIG. 21). Analysis was performed for the following cancer types in the same manner.

Figure 22A:
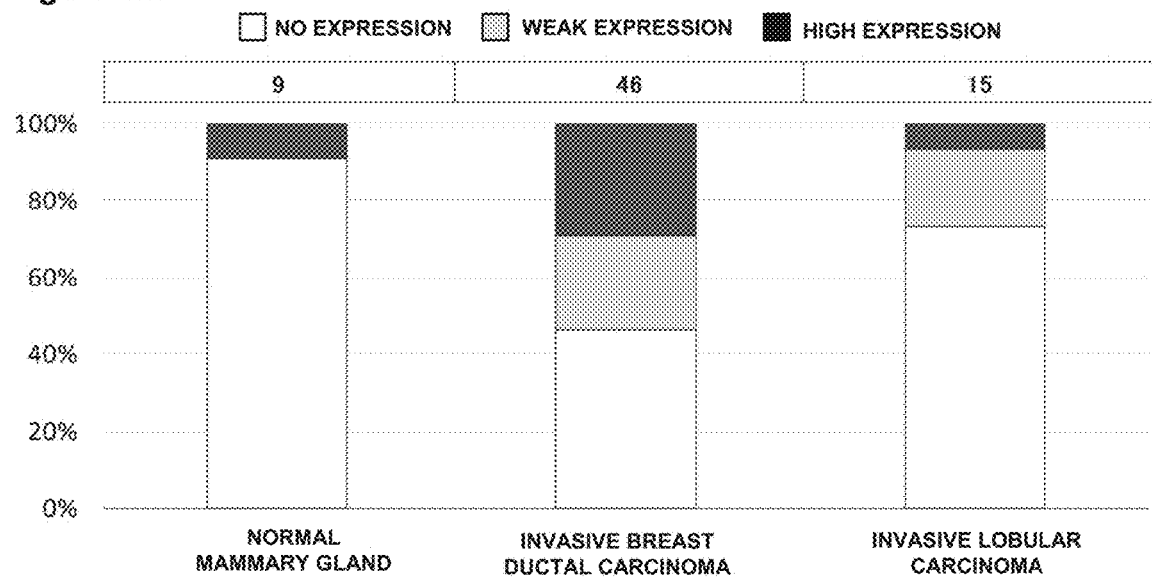
FIG. 22 is a diagram illustrating an expression analysis result in a mammary gland. (A) shows a CHRNB2 expression profile, and (B) shows an NPTXR expression profile.
Figure 22B:
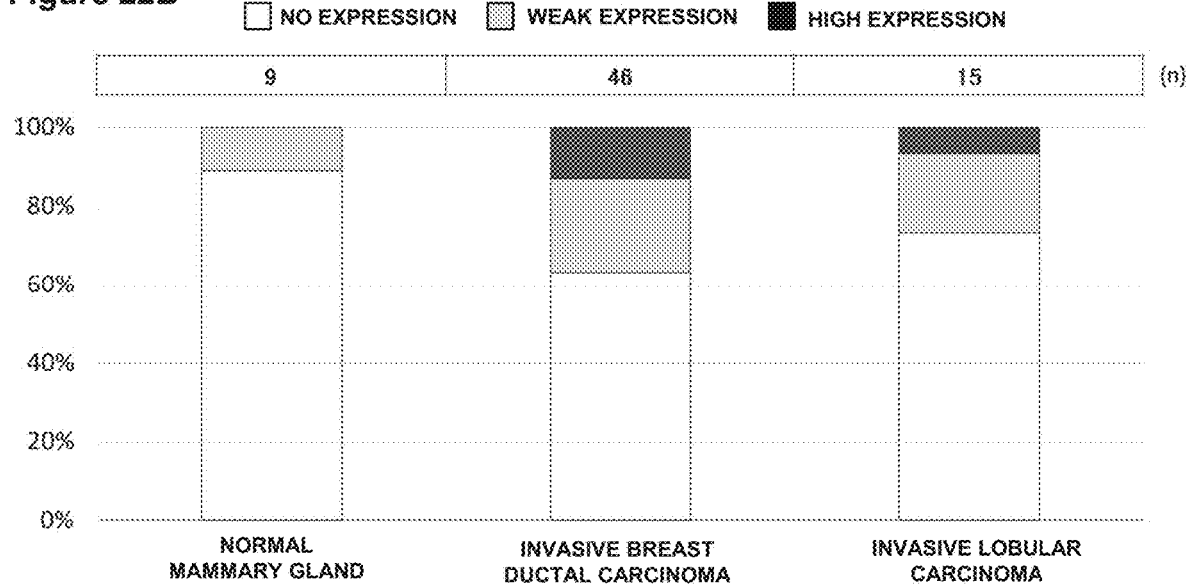
Figure 23A:
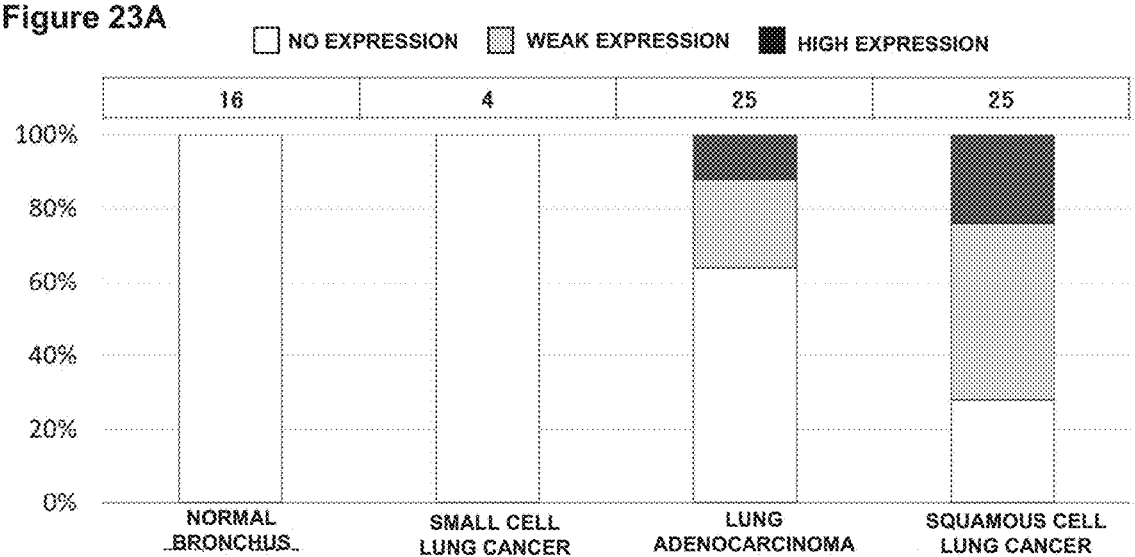
FIG. 23 is a diagram illustrating an expression analysis result in a lung. (A) shows a CHRNB2 expression profile, and (B) shows an NPTXR expression profile.
Figure 23B:
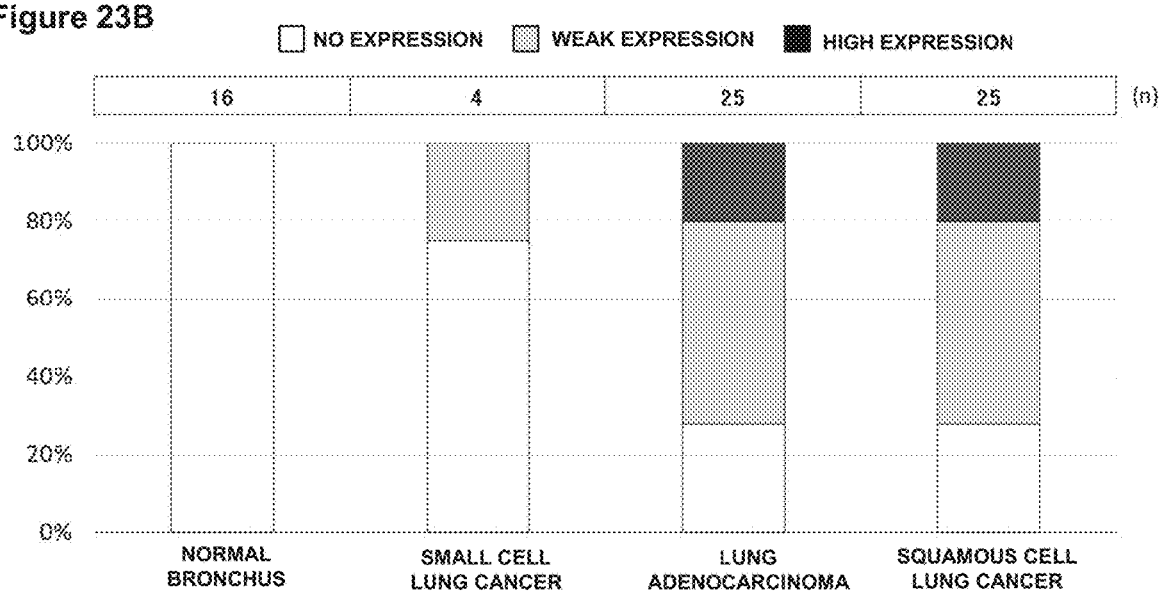
Figure 24A:
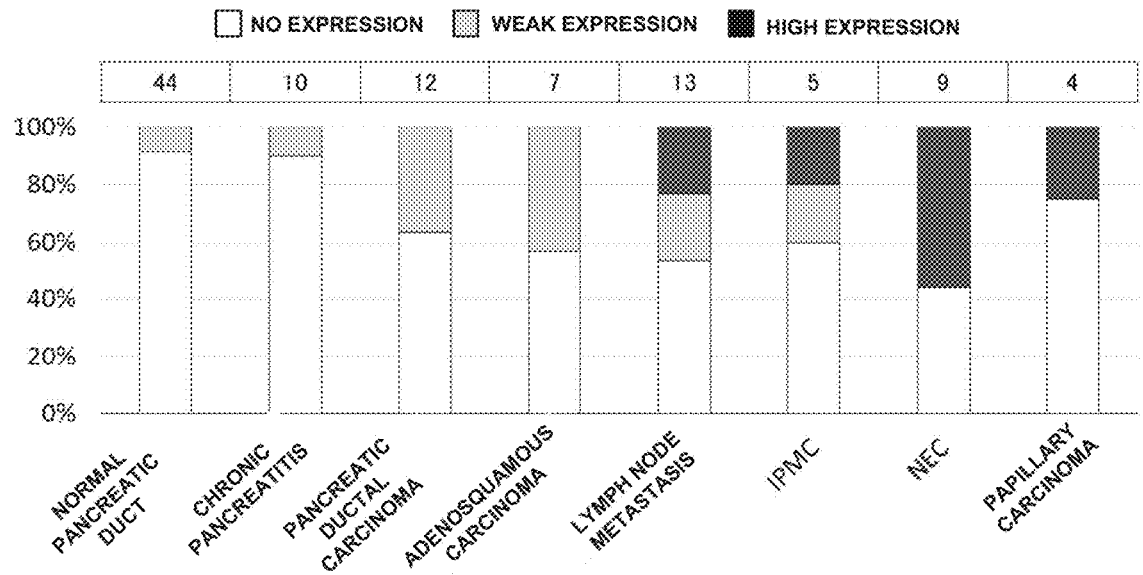
FIG. 24 is a diagram illustrating an expression analysis result in a pancreas. (A) shows a CHRNB2 expression profile, and (B) shows an NPTXR expression profile.
Figure 24B:
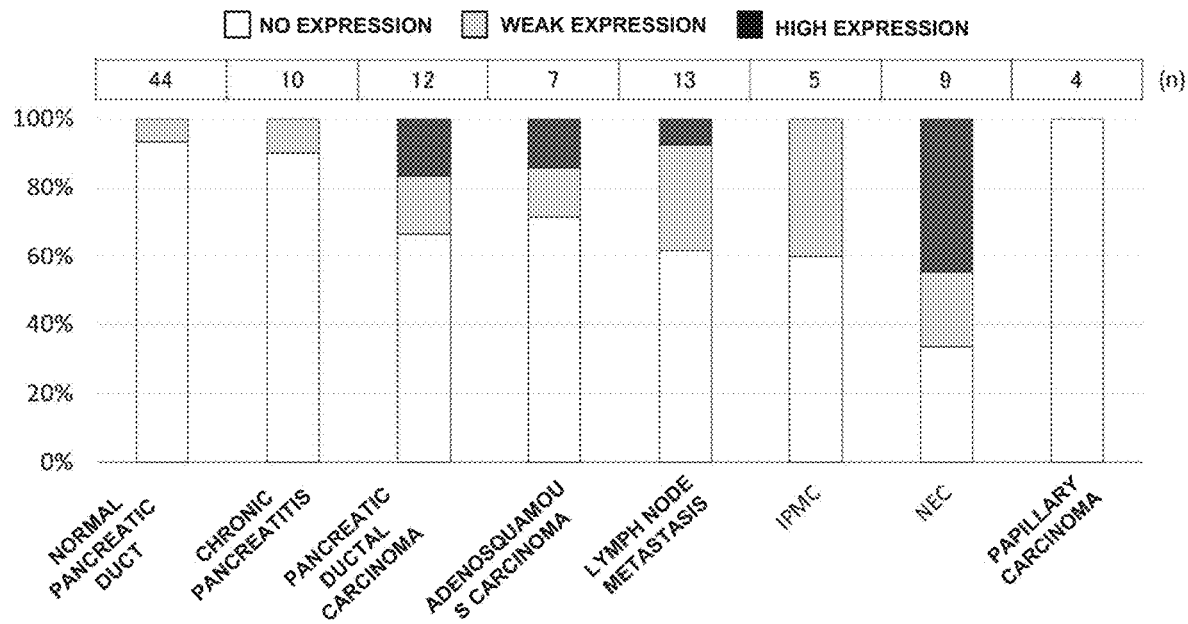
Figure 25A:
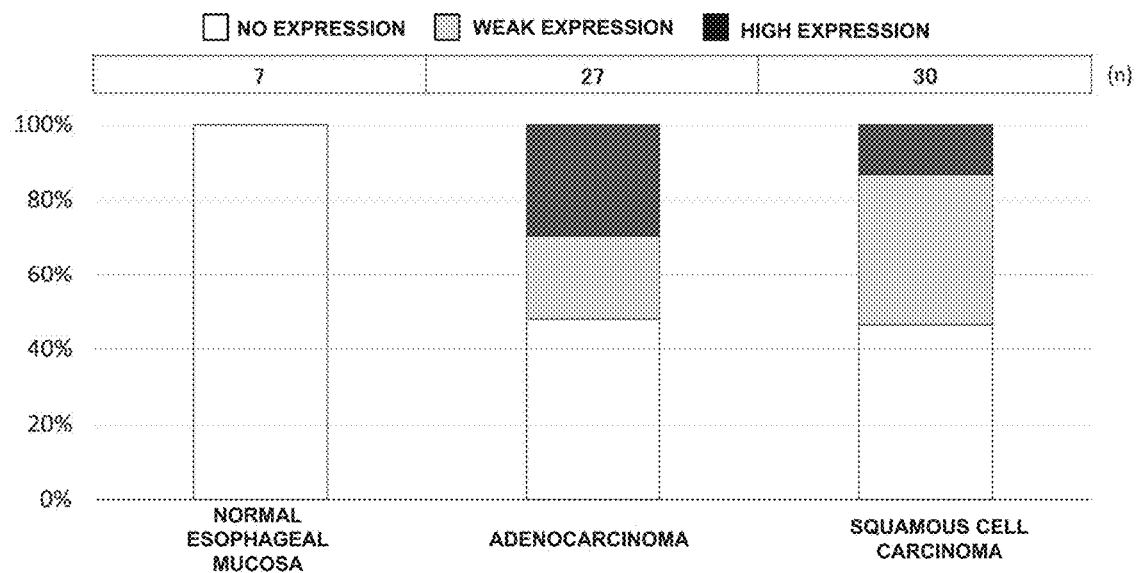
FIG. 25 is a diagram illustrating an expression analysis result in an esophagus. (A) shows a CHRNB2 expression profile, and (B) shows an NPTXR expression profile.
Figure 25B:
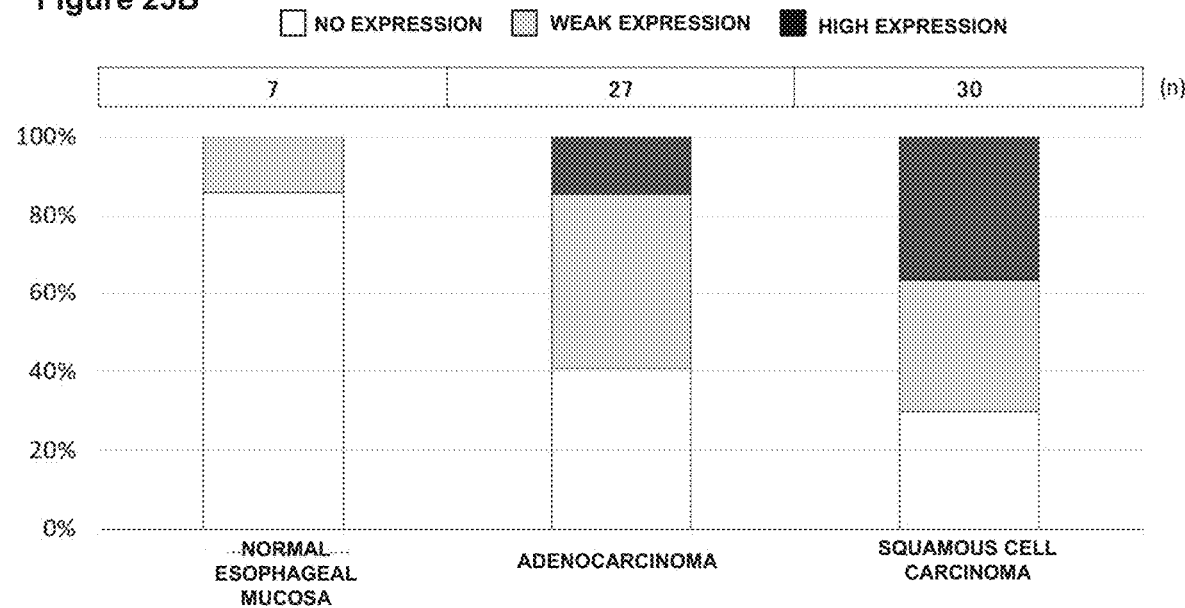

The CHRNB2 expression analysis and the NPTXR expression analysis in breast cancer were performed (FIG. 22). The CHRNB2 expression was observed in approximately 40% of breast cancer, and the NPTXR expression was observed in approximately 30% of breast cancer. The CHRNB2 expression analysis and the NPTXR expression analysis in lung cancer were performed (FIG. 23). Both the CHRNB2 expression and the NPTXR expression were observed in approximately 50% of lung cancer. The CHRNB2 expression analysis and the NPTXR expression analysis in pancreatic cancer were performed (FIG. 24). The CHRNB2 expression was observed in approximately 40% of pancreatic cancer, and the NPTXR expression was observed in approximately 50% of pancreatic cancer. The CHRNB2 expression analysis and the NPTXR expression analysis in esophageal cancer were performed (FIG. 25). Both the CHRNB2 expression and the NPTXR expression were observed in approximately 50% of esophageal cancer.

According to the result of the tissue array described above, the CHRNB2 expression and the NPTXR expression are low in the normal tissue and are observed not only in the stomach cancer but also in various types of cancers such as breast cancer, lung cancer, pancreatic cancer, esophageal cancer, and the like. It was therefore implied that treatment can also be performed for these cancers by an inhibitor that inhibits CHRNB2 expression or NPTXR expression or an antibody medicine that binds to CHRNB2 or NPTXR.

INDUSTRIAL APPLICABILITY

A high CHRNB2 expression group and a high NPTXR expression group were found from case groups in which S-post-operative supplemental therapy regarded as standard therapy was administered. Therefore, these two molecules are the molecules to be a key to overcome the situation that was unable to be controlled by the existing therapy. The medicine that neutralizes or inhibits expression of CHRNB2 or NPTXR is totally different in the target from the existing molecular target therapeutic drug mainly associated with growth factor receptors. Therefore, the medicine becomes a completely novel therapeutic drug. Further, such a medicine may be the medicine that has the effect on a tumor with high CHRNB2 or NPTXR expression without limited to stomach cancer.

The invention claimed is:

1. A method of treating cancer in a patient, the method comprising administering to the patient a therapeutically effective amount of an anti-neuronal pentraxin receptor (NPTXR) antibody having three heavy chain complementarity determining regions (HCDR1, HCDR2, and HCDR3) and three light chain complementarity determining regions (LCDR1, LCDR2, and LCDR3) of an antibody produced by a hybridoma deposited with NITE Patent Microorganisms Depositary (NPMD) and assigned with Accession No. NITE BP-02856,
wherein the anti-NPTXR antibody binds specifically to NPTXR and inhibits NPTXR function, and
wherein the cancer expresses the NPTXR and is selected from stomach cancer, colorectal cancer, breast cancer, pancreatic cancer, and esophageal cancer.

2. The method according to claim 1, wherein the cancer comprises a tumor with high NPTXR expression.

3. The method according to claim 1, wherein the anti-NPTXR antibody is produced by the hybridoma assigned with Accession No. NITE BP-02856.

4. The method according to claim 1, further comprising a step of testing NPTXR expression by using a test kit,
wherein the test kit comprises an antibody that recognizes NPTXR or a primer that quantifies mRNA expression of NPTXR; and a reagent required for measurement.

5. The method according to claim 1, wherein the anti-NPTXR antibody recognizes an amino acid sequence selected from the group consisting of CESGLPR-GLQGAGPRRDT (SEQ ID NO: 10), KERVALSHSSR-RORQEVE (SEQ ID NO: 11), and SEQ ID NO: 12 (GLPR-GLQGAGPRRDT).

6. The method of claim 1, wherein the anti-NPTXR antibody comprises a heavy chain variable region (HCVR) and a light chain variable region (LCVR) of an antibody produced by a hybridoma deposited with NPMD and assigned with Accession No. NITE BP-02856.

* * * * *

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: PCR primer

<400> SEQUENCE: 1
agcgaggacg atgaccag                                                 18

<210> SEQ ID NO 2
<211> LENGTH: 20
<212> TYPE: DNA
<213> ORGANISM: Artificial Sequence
<220> FEATURE:
<223> OTHER INFORMATION: PCR preimer

<400> SEQUENCE: 2
ggtgccaaag acacagacaa                                               20

<210> SEQ ID NO 3
<211> LENGTH: 20
<212> TYPE: DNA
<213> ORGANISM: Artificial Sequence
<220> FEATURE:
<223> OTHER INFORMATION: PCR primer
```

```
<400> SEQUENCE: 3
tcattctgga gctggaggac                                                    20

<210> SEQ ID NO 4
<211> LENGTH: 19
<212> TYPE: DNA
<213> ORGANISM: Artificial Sequence
<220> FEATURE:
<223> OTHER INFORMATION: PCR primer

<400> SEQUENCE: 4
ggcagctgag aggttcaca                                                     19

<210> SEQ ID NO 5
<211> LENGTH: 19
<212> TYPE: DNA
<213> ORGANISM: Artificial Sequence
<220> FEATURE:
<223> OTHER INFORMATION: PCR primer

<400> SEQUENCE: 5
gaaggtgaag gtcggagtc                                                     19

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
gaagatggtg atgggatttc                                                    20

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
caagcttccc gttctcagcc                                                    20

<210> SEQ ID NO 8
<211> LENGTH: 18
<212> TYPE: PRT
<213> ORGANISM: Artificial Sequence
<220> FEATURE:
<223> OTHER INFORMATION: CHRNB2_#94-111

<400> SEQUENCE: 8

Trp Lys Pro Glu Glu Phe Asp Asn Met Lys Lys Val Arg Leu Pro Ser
1               5                   10                  15

Lys His

<210> SEQ ID NO 9
<211> LENGTH: 13
<212> TYPE: PRT
<213> ORGANISM: Artificial Sequence
<220> FEATURE:
<223> OTHER INFORMATION: CHRNB2_#490-502

<400> SEQUENCE: 9

Thr Phe Leu His Ser Asp His Ser Ala Pro Ser Ser Lys
```

```
<210> SEQ ID NO 10
<211> LENGTH: 18
<212> TYPE: PRT
<213> ORGANISM: Artificial Sequence
<220> FEATURE:
<223> OTHER INFORMATION: NPTXR_#161-178

<400> SEQUENCE: 10

Cys Glu Ser Gly Leu Pro Arg Gly Leu Gln Gly Ala Gly Pro Arg Arg
1               5                   10                  15
Asp Thr

<210> SEQ ID NO 11
<211> LENGTH: 18
<212> TYPE: PRT
<213> ORGANISM: Artificial Sequence
<220> FEATURE:
<223> OTHER INFORMATION: NPTXR_#251-268

<400> SEQUENCE: 11

Lys Glu Arg Val Ala Leu Ser His Ser Ser Arg Arg Gln Arg Gln Glu
1               5                   10                  15
Val Glu

<210> SEQ ID NO 12
<211> LENGTH: 15
<212> TYPE: PRT
<213> ORGANISM: Artificial Sequence
<220> FEATURE:
<223> OTHER INFORMATION: NH-01 epitope

<400> SEQUENCE: 12

Gly Leu Pro Arg Gly Leu Gln Gly Ala Gly Pro Arg Arg Asp Thr
1               5                   10                  15
```